US005916204A

United States Patent [19]
Milani

[11] Patent Number: 5,916,204
[45] Date of Patent: Jun. 29, 1999

[54] METHOD OF FORMING A PARTICLE SIZE GRADIENT IN AN ABSORBENT ARTICLE

[75] Inventor: John Milani, Alpharetta, Ga.

[73] Assignee: Kimberly-Clark Worldwide, Inc., Neenah, Wis.

[21] Appl. No.: 09/013,325

[22] Filed: Jan. 26, 1998

Related U.S. Application Data

[62] Division of application No. 08/878,298, Jun. 18, 1997, Pat. No. 5,807,366, which is a continuation of application No. 08/351,966, Dec. 8, 1994, abandoned.

[51] Int. Cl.$^6$ .............................. A61F 13/15; B32B 31/00; B05D 1/32; B05D 1/06
[52] U.S. Cl. ................... 604/368; 156/272.6; 156/273.1; 427/466; 427/469
[58] Field of Search ................................ 604/368, 385.1, 604/358; 156/272.6, 273.1, 276; 427/466, 469, 470

[56] References Cited

U.S. PATENT DOCUMENTS

| | | |
|---|---|---|
| Re. 30,782 | 10/1981 | van Turnhout . |
| Re. 31,285 | 6/1983 | van Turnhout et al. . |
| Re. 32,171 | 6/1986 | van Turnhout . |
| 668,791 | 2/1901 | Blake et al. . |
| 813,063 | 2/1906 | Sutton et al. . |
| 859,998 | 7/1907 | Wentworth . |
| 924,032 | 6/1909 | Blake et al. . |
| 1,222,305 | 4/1917 | Kraus . |
| 1,297,159 | 3/1919 | Hedberg . |
| 1,355,477 | 10/1920 | Howell . |
| 2,106,865 | 2/1938 | Bantz et al. . |
| 2,217,444 | 10/1940 | Hill . |
| 2,328,577 | 9/1943 | Oglesby . |
| 2,378,067 | 3/1945 | Cook, Jr. . |
| 2,398,792 | 4/1946 | Johnson . |
| 2,748,018 | 5/1956 | Miller . |
| 2,998,051 | 8/1961 | Sittel . |
| 3,012,668 | 12/1961 | Fraas . |
| 3,059,772 | 10/1962 | Baron . |
| 3,125,547 | 3/1964 | Blatz . |
| 3,281,347 | 10/1966 | Winder . |
| 3,323,933 | 6/1967 | Barford et al. . |
| 3,338,992 | 8/1967 | Kinney . |
| 3,341,007 | 9/1967 | Mayer, Jr. et al. . |
| 3,341,394 | 9/1967 | Kinney . |
| 3,380,584 | 4/1968 | Fulwyler . |
| 3,402,814 | 9/1968 | Morel et al. . |
| 3,436,797 | 4/1969 | Graf et al. . |
| 3,502,763 | 3/1970 | Hartmann . |
| 3,542,615 | 11/1970 | Dobo et al. . |
| 3,581,886 | 6/1971 | Singewald et al. . |
| 3,692,606 | 9/1972 | Miller et al. . |
| 3,692,618 | 9/1972 | Dorschner et al. . |
| 3,802,817 | 4/1974 | Matsuki et al. . |
| 3,821,021 | 6/1974 | McMillan . |
| 3,849,241 | 11/1974 | Butin et al. . |
| 3,855,046 | 12/1974 | Hansen et al. . |
| 3,859,330 | 1/1975 | Proskow . |
| 3,896,802 | 7/1975 | Williams . |
| 3,907,604 | 9/1975 | Prentice . |
| 3,909,009 | 9/1975 | Cvetko et al. . |
| 3,962,386 | 6/1976 | Driscoll . |
| 3,979,529 | 9/1976 | Rebentisch et al. . |
| 3,998,916 | 12/1976 | van Turnhout . |
| 4,011,067 | 3/1977 | Carey, Jr. . |
| 4,013,816 | 3/1977 | Sabee et al. . |
| 4,035,164 | 7/1977 | Taylor . |
| 4,041,203 | 8/1977 | Brock et al. . |
| 4,058,724 | 11/1977 | McKinney et al. . |
| 4,070,218 | 1/1978 | Weber . |
| 4,091,140 | 5/1978 | Harrnon . |
| 4,096,289 | 6/1978 | Nischwitz et al. . |
| 4,103,062 | 7/1978 | Aberson et al. . |
| 4,140,607 | 2/1979 | Kreiseimeier et al. . |
| 4,170,304 | 10/1979 | Huke . |
| 4,178,157 | 12/1979 | van Turnhout et al. . |
| 4,185,972 | 1/1980 | Nitta et al. . |
| 4,196,245 | 4/1980 | Kitson et al. . |
| 4,208,366 | 6/1980 | Kinney . |
| 4,209,563 | 6/1980 | Sisson . |
| 4,215,682 | 8/1980 | Kubik et al. . |
| 4,223,677 | 9/1980 | Anderson . |
| 4,273,635 | 6/1981 | Beraud et al. . |
| 4,298,440 | 11/1981 | Hood . |
| 4,305,797 | 12/1981 | Knoll et al. . |
| 4,307,143 | 12/1981 | Meitner . |
| 4,308,223 | 12/1981 | Stern . |
| 4,310,478 | 1/1982 | Balslev et al. . |
| 4,323,374 | 4/1982 | Shinagawa et al. . |

5,916,204
Page 2

| | | |
|---|---|---|
| 4,324,198 | 4/1982 | Muz . |
| 4,340,563 | 7/1982 | Appel et al. . |
| 4,342,812 | 8/1982 | Selwood . |
| 4,353,799 | 10/1982 | Leonard . |
| 4,357,234 | 11/1982 | Inculet et al. . |
| 4,363,682 | 12/1982 | Thiebault . |
| 4,363,723 | 12/1982 | Knoll et al. . |
| 4,373,224 | 2/1983 | Bandai et al. . |
| 4,374,727 | 2/1983 | Takahashi et al. . |
| 4,374,888 | 2/1983 | Bornslaeger . |
| 4,375,718 | 3/1983 | Wadsworth et al. . |
| 4,392,876 | 7/1983 | Schmidt . |
| 4,394,235 | 7/1983 | Brandt et al. . |
| 4,411,795 | 10/1983 | Olson . |
| 4,430,277 | 2/1984 | Lin . |
| 4,443,513 | 4/1984 | Meitner et al. . |
| 4,443,515 | 4/1984 | Atlas . |
| 4,451,589 | 5/1984 | Morman et al. . |
| 4,455,195 | 6/1984 | Kinsley . |
| 4,455,237 | 6/1984 | Kinsley . |
| 4,456,648 | 6/1984 | Adamse et al. . |
| 4,492,633 | 1/1985 | Sandulyak et al. . |
| 4,507,539 | 3/1985 | Sando et al. . |
| 4,513,049 | 4/1985 | Yamasaki et al. . |
| 4,514,289 | 4/1985 | Inculet . |
| 4,517,143 | 5/1985 | Kisler . |
| 4,534,918 | 8/1985 | Forrest, Jr. . |
| 4,547,420 | 10/1985 | Krueger et al. . |
| 4,551,378 | 11/1985 | Carey, Jr. . |
| 4,554,207 | 11/1985 | Lee . |
| 4,555,811 | 12/1985 | Shimalla . |
| 4,588,537 | 5/1986 | Klaase et al. . |
| 4,592,815 | 6/1986 | Nakao . |
| 4,594,626 | 6/1986 | Frangesh . |
| 4,618,524 | 10/1986 | Groitzsch et al. . |
| 4,622,259 | 11/1986 | McAmish et al. . |
| 4,623,438 | 11/1986 | Felton et al. . |
| 4,626,263 | 12/1986 | Inoue et al. . |
| 4,652,282 | 3/1987 | Ohmori et al. . |
| 4,652,322 | 3/1987 | Lim . |
| 4,657,639 | 4/1987 | Mahadevan et al. . |
| 4,657,804 | 4/1987 | Mays et al. . |
| 4,663,220 | 5/1987 | Wisneski . |
| 4,670,913 | 6/1987 | Morell et al. . |
| 4,671,943 | 6/1987 | Wahlquist . |
| 4,677,017 | 6/1987 | DeAntonis et al. . |
| 4,689,241 | 8/1987 | Richart et al. . |
| 4,699,823 | 10/1987 | Kellenberger et al. . |
| 4,705,151 | 11/1987 | Eldridge . |
| 4,707,398 | 11/1987 | Boggs . |
| 4,720,415 | 1/1988 | VanderWielen et al. . |
| 4,729,371 | 3/1988 | Krueger et al. . |
| 4,738,772 | 4/1988 | Giesfeldt . |
| 4,739,882 | 4/1988 | Parikh et al. . |
| 4,749,348 | 6/1988 | Klaase et al. . |
| 4,761,326 | 8/1988 | Barnes et al. . |
| 4,789,504 | 12/1988 | Ohmori et al. . |
| 4,795,668 | 1/1989 | Krueger et al. . |
| 4,797,201 | 1/1989 | Kuppers et al. . |
| 4,797,318 | 1/1989 | Brooker et al. . |
| 4,818,464 | 4/1989 | Lau . |
| 4,826,703 | 5/1989 | Kisler . |
| 4,831,664 | 5/1989 | Suda . |
| 4,847,914 | 7/1989 | Suda . |
| 4,859,266 | 8/1989 | Akasaki et al. . |
| 4,863,785 | 9/1989 | Berman et al. . |
| 4,863,983 | 9/1989 | Johnson et al. . |
| 4,874,399 | 10/1989 | Reed et al. . |
| 4,874,659 | 10/1989 | Ando et al. . |
| 4,883,052 | 11/1989 | Weiss et al. . |
| 4,886,527 | 12/1989 | Fottinger et al. . |
| 4,894,131 | 1/1990 | Jacobs et al. . |
| 4,901,370 | 2/1990 | Suda . |
| 4,904,174 | 2/1990 | Moosmayer et al. . |
| 4,917,942 | 4/1990 | Winters . |
| 4,920,168 | 4/1990 | Nohr et al. . |
| 4,944,854 | 7/1990 | Felton et al. . |
| 4,948,515 | 8/1990 | Okumura et al. . |
| 4,948,639 | 8/1990 | Brooker et al. . |
| 4,960,820 | 10/1990 | Hwo . |
| 4,965,122 | 10/1990 | Morman . |
| 4,983,677 | 1/1991 | Johnson et al. . |
| 5,012,094 | 4/1991 | Hamade . |
| 5,021,501 | 6/1991 | Ohmori et al. . |
| 5,032,419 | 7/1991 | Lamirand et al. . |
| 5,035,941 | 7/1991 | Blackburn . |
| 5,051,159 | 9/1991 | Togashi et al. . |
| 5,055,151 | 10/1991 | Duffy . |
| 5,057,710 | 10/1991 | Nishiura et al. . |
| 5,062,158 | 11/1991 | Oka et al. . |
| 5,077,468 | 12/1991 | Hamade . |
| 5,090,975 | 2/1992 | Requejo et al. . |
| 5,110,620 | 5/1992 | Tani et al. . |
| 5,112,048 | 5/1992 | Deeds . |
| 5,112,677 | 5/1992 | Tani et al. . |
| 5,118,942 | 6/1992 | Hamade . |
| 5,135,724 | 8/1992 | Dinter et al. . |
| 5,138,971 | 8/1992 | Nakajima et al. . |
| 5,143,767 | 9/1992 | Matsuura et al. . |
| 5,149,335 | 9/1992 | Kellenberger et al. . |
| 5,156,902 | 10/1992 | Pieper et al. . |
| 5,165,979 | 11/1992 | Watkins et al. . |
| 5,169,706 | 12/1992 | Collier, IV et al. . |
| 5,173,356 | 12/1992 | Eaton et al. . |
| 5,178,932 | 1/1993 | Perkins et al. . |
| 5,183,701 | 2/1993 | Jacobs et al. . |
| 5,188,885 | 2/1993 | Timmons et al. . |
| 5,204,174 | 4/1993 | Daponte et al. . |
| 5,206,061 | 4/1993 | Ando et al. . |
| 5,213,881 | 5/1993 | Timmons et al. . |
| 5,213,882 | 5/1993 | Sassa et al. . |
| 5,226,992 | 7/1993 | Morman . |
| 5,230,727 | 7/1993 | Pound et al. . |
| 5,232,770 | 8/1993 | Joseph . |
| 5,238,733 | 8/1993 | Joseph et al. . |
| 5,244,482 | 9/1993 | Hassenboehler, Jr. . |
| 5,246,637 | 9/1993 | Matsuura et al. . |
| 5,247,072 | 9/1993 | Ning et al. . |
| 5,254,297 | 10/1993 | Deeds . |
| 5,256,176 | 10/1993 | Matsuura et al. . |
| 5,257,982 | 11/1993 | Cohen et al. . |
| 5,264,276 | 11/1993 | McGregor et al. . |
| 5,284,703 | 2/1994 | Everhart et al. . |
| 5,286,326 | 2/1994 | Greve . |
| 5,294,482 | 3/1994 | Gessner . |
| 5,306,534 | 4/1994 | Bosses . |
| 5,308,674 | 5/1994 | Zafiroglu . |
| 5,308,691 | 5/1994 | Lim et al. . |
| 5,336,545 | 8/1994 | Morman . |
| 5,350,620 | 9/1994 | Sundet et al. . |
| 5,389,202 | 2/1995 | Everhart et al. . |
| 5,397,413 | 3/1995 | Trimble et al. . |
| 5,401,446 | 3/1995 | Tsai et al. . |
| 5,407,581 | 4/1995 | Onodera et al. . |
| 5,409,766 | 4/1995 | Yuasa et al. . |
| 5,411,576 | 5/1995 | Jones et al. . |
| 5,436,033 | 7/1995 | Mino et al. . |
| 5,436,066 | 7/1995 | Chen . |
| 5,441,550 | 8/1995 | Hassenboehler, Jr. . |
| 5,443,606 | 8/1995 | Hassenboehler, Jr. . |
| 5,455,108 | 10/1995 | Quincy et al. . |
| 5,456,972 | 10/1995 | Roth et al. . |
| 5,464,688 | 11/1995 | Timmons et al. . |
| 5,468,428 | 11/1995 | Hanschen et al. . |

| | | |
|---|---|---|
| 5,472,481 | 12/1995 | Jones et al. . |
| 5,482,765 | 1/1996 | Bradley et al. . |
| 5,486,411 | 1/1996 | Hassenboehler, Jr. et al. . |
| 5,491,022 | 2/1996 | Smith . |
| 5,493,117 | 2/1996 | Tamaki et al. . |
| 5,496,507 | 3/1996 | Angadjivand et al. . |
| 5,503,745 | 4/1996 | Ogata et al. . |

FOREIGN PATENT DOCUMENTS

| | | |
|---|---|---|
| 1188452 | 6/1985 | Canada . |
| 0 125 851 | 11/1984 | European Pat. Off. . |
| 0 156 160 | 10/1985 | European Pat. Off. . |
| 0 334 829 | 9/1989 | European Pat. Off. . |
| 0 337 662 | 10/1989 | European Pat. Off. . |
| 0 375 234 | 6/1990 | European Pat. Off. . |
| 0 391 725 | 10/1990 | European Pat. Off. . |
| 0 444 671 | 9/1991 | European Pat. Off. . |
| 0 462 574 | 12/1991 | European Pat. Off. . |
| 0 478 011 | 4/1992 | European Pat. Off. . |
| 0 497 072 | 8/1992 | European Pat. Off. . |
| 0 520 798 | 12/1992 | European Pat. Off. . |
| 0 550 029 | 7/1993 | European Pat. Off. . |
| 0 575 629 | 12/1993 | European Pat. Off. . |
| 0 576 738 | 1/1994 | European Pat. Off. . |
| 0 594 123 | 4/1994 | European Pat. Off. . |
| 1084015 | 9/1957 | Germany . |
| 44 47 152 | 7/1995 | Germany . |
| 58-076118 | 7/1958 | Japan . |
| 62-053719 | 8/1987 | Japan . |
| 62-074423 | 9/1987 | Japan . |
| 1-246413 | 10/1989 | Japan . |
| 5-064713 | 3/1993 | Japan . |
| 2 026 379 | 2/1980 | United Kingdom . |
| 2 242 142 | 9/1991 | United Kingdom . |
| 81/03265 | 11/1981 | WIPO . |
| 90/11784 | 10/1990 | WIPO . |
| 91/08254 | 6/1991 | WIPO . |
| 92/16681 | 10/1992 | WIPO . |
| 93/06168 | 4/1993 | WIPO . |
| 93/09156 | 5/1993 | WIPO . |
| 94/00166 | 1/1994 | WIPO . |
| 94/01068 | 1/1994 | WIPO . |
| 95/05232 | 2/1995 | WIPO . |
| 95/05501 | 2/1995 | WIPO . |
| 96/28597 | 9/1996 | WIPO . |

OTHER PUBLICATIONS

Database WPI, Section Ch, Week 8930, Derwent Publications, Ltd., London, GB; Class A94, AN 89–217687 XP002005648 & JP,A,01 156 578 (Showa Denko), Jun. 20, 1989, See Abstract.

IBM Technical Disclosure Bulletin, vol. 14, No. 12, May 1972, "Bonding Process".

Database WPI, Section Ch, Week 8428, Derwent Publications Ltd., London, GB; Class A87, AN 84–173431, XP002008760, & JP,A,59 094 621 (Unitika KK), May 31, 1984, see abstract.

Patent Abstracts of Japan, vol. 10, No. 71 (C–334), Mar. 20, 1986 & JP,A,60 209220 (Kouken K.K.), Oct. 21, 1985, see abstract.

Patent Abstracts of Japan, vol. 6, No. 191 (C–127), Sep. 30, 1982 & JP,A,57 105217 (Nitta K.K.), Jun. 30, 1982, see abstract & Chemical Abstracts, vol. 97, No. 26, Dec. 27, 1982, Columbus, Ohio, US; abstract No. 218901, "Fibrous Filtering Material", see abstract.

Patent Abstracts of Japan, vol. 11, No. 315 (C–451), Oct. 14, 1987 & JP,A,62 102809 (Mitsui Petrochem. Ind. Ltd.), May 13, 1987, see abstract & Database WPI, Section Ch, Week 8725, Derwent Publications Ltd., London, GB; Class A12, AN 87–172842 & JP,A,62 102 809 (Mitsui Petrochem. Ind. Co. Ltd.), May 13, 1987, see abstract.

Journal of Electrostatics, vol. 21, 1988, Amsterdam NL, pp. 81–98, XP002012022, P. A. Smith & G. C. East: "Generation of Triboelectric Charge in Textile Fibre Mistures, and their use as Air Filters", see document.

An Introduction to Electrostatic Separation, Technical Bulletin Bulletin 8570, Carpco, Inc.

*Electrostatic Separation of Mixed Granular Solids* by Oliver C. Ralston, Elsevier Publishing Company, 1961, Chapter IV, "Applications of Electrostatic Separation", pp. 134–234.

J. van Turnhout: Topics in Applied Physics, vol. 33, Chapter 3 "Thermally Stimulated Discharge of Electrets", pp. 81–215 (1980).

J. van Turnhout: Thermally Stimulated Discharge of Polymer Electrets, Chapter 1, pp. 1–24 (1975).

G.M. Sessler: Electronic Properties of Polymers, Chapter 3 "Charge Storage", pp. 59–107.

USSN 08/242,948 filed May 16, 1994 entitled "Nonwoven Absorbent Polymeric Fabric Exhibiting Improved Fluid Management And Methods For Making The Same".

*Primary Examiner*—John G. Weiss
*Assistant Examiner*—Dennis Ruhl
*Attorney, Agent, or Firm*—David J. Alexander; Nancy M. Klembus

[57] ABSTRACT

An absorbent structure containing an absorbent particle size gradient is disclose. The absorbent structure may also include a fiber size gradient. The absorbent structure may also include absorbent particles coupled to loosely distributed fibers and more particularly, the absorbent particles may be electrostatically couple to the loosely distributed fibers.

3 Claims, 10 Drawing Sheets

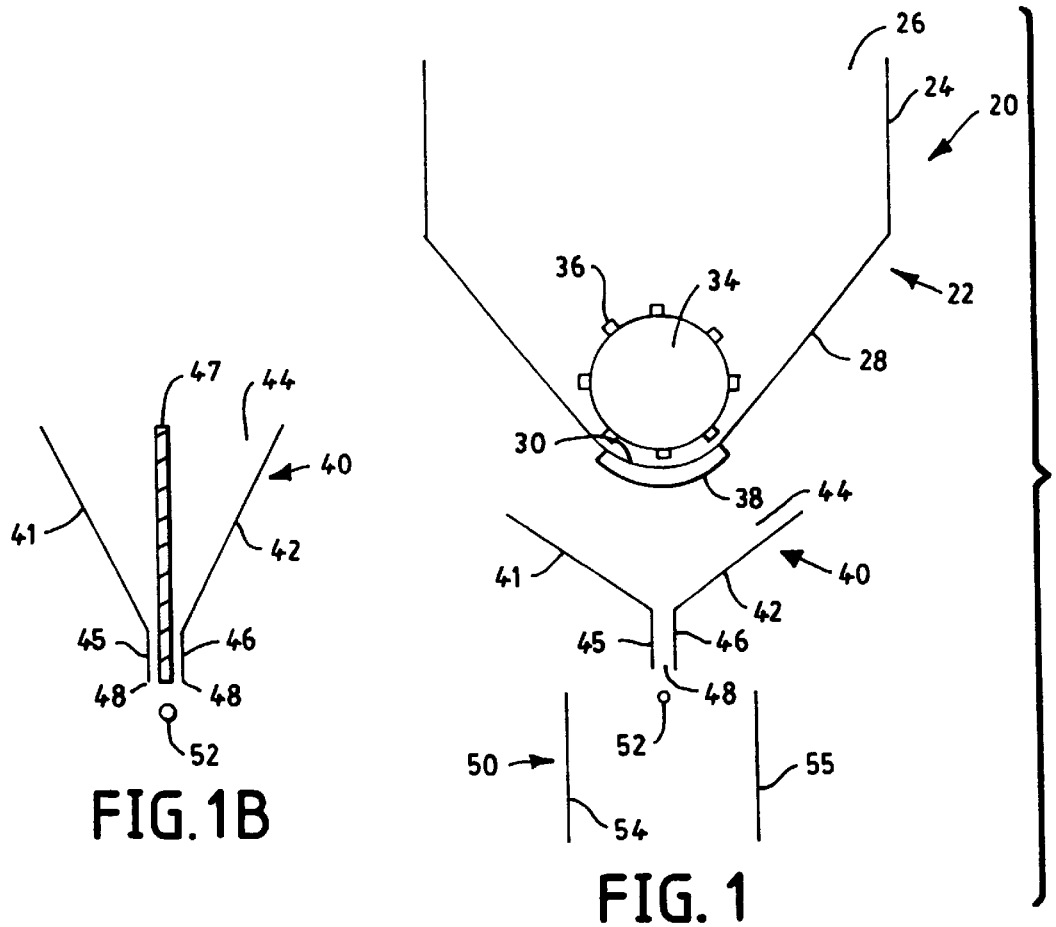
FIG. 1B
FIG. 1
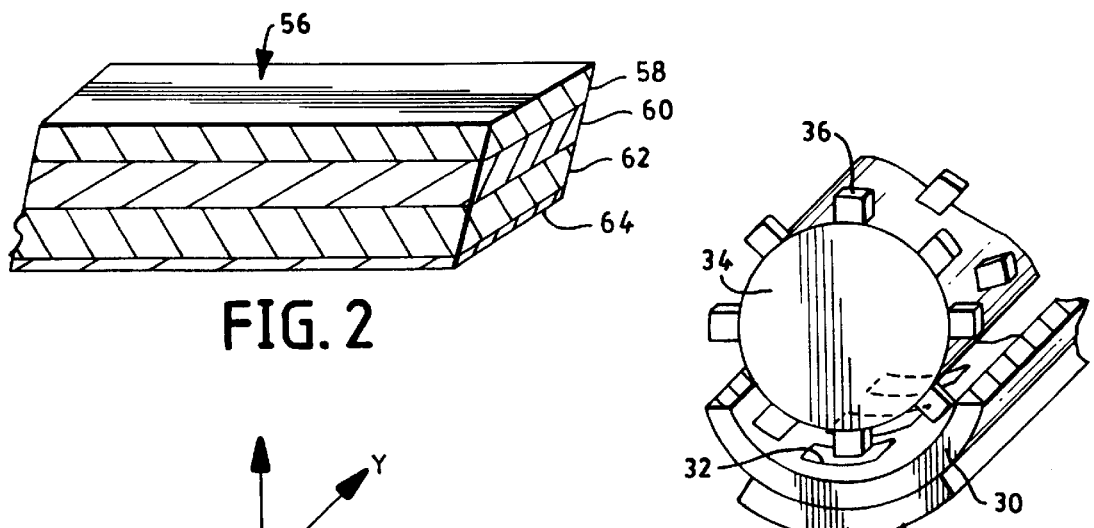
FIG. 2
FIG. 1A
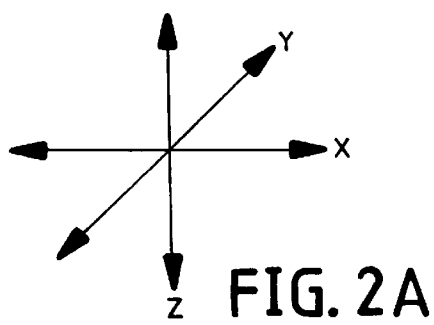
FIG. 2A

METHOD OF FORMING A PARTICLE SIZE GRADIENT IN AN ABSORBENT ARTICLE

This application is a divisional of application Ser. No. 08/878,298 entitled METHOD OF FORMING A PARTICLE SIZE GRADIENT IN AN ABSORBENT ARTICLE and filed in the U.S. Patent and Trademark Office on Jun. 18, 1997, now U.S. Pat. No. 5,807,366 which is a continuation of application Ser. No. 08/351,966 entitled METHOD OF FORMING A PARTICLE SIZE GRADIENT IN AN ABSORBENT ARTICLE and filed in the U.S. Patent and Trademark Office on Dec. 8, 1994 now abandoned. The entirety of the applications having Ser. Nos. 08/878,298 and 08/351,966 is hereby incorporated by reference.

FIELD OF THE INVENTION

This invention relates to absorbent articles and methods of making the same. More particularly, the present invention relates to absorbent articles which include absorbent particles.

BACKGROUND OF THE INVENTION

Disposable absorbent articles such as, for example, incontinence products, infant and adolescent care products such as diapers, and feminine care products are generally designed with various layers for performing different liquid management functions. These functions include surge control, distribution of liquids, liquid absorption and retention and liquid barrier. To improve the overall liquid management of these products and other liquid absorbent articles, considerable time, effort and expense have been directed to improving the performance of the materials which are used to form one or more of these layers.

The overall liquid management of an absorbent product may be considered to be the product's ability to not only absorb a liquid but also to transport or channel the absorbed liquid to a desired location within the absorbent article for storage. For example, in products such as diapers and feminine care products, liquid retention at the interface between the body and the product is generally not desired. It is generally desired that such products be designed to rapidly uptake and draw such liquids away from the body/product interface. A material layer which rapidly uptakes a liquid and moves the liquid away from the body/product interface is sometimes referred to as a surge layer or surge structure. Once the liquid has been drawn away from the body/product interface, the liquid is desirably channeled, via a distribution layer, toward and into one or more storage layers. These storage layers desirably hold or contain such liquid while minimizing reabsorption of the liquid by the surge layer. A barrier layer adjacent the storage layer functions to contain the stored liquid within the product.

The storage layer, for example, may be formed from fibers or a combination of fibers and absorbent particles. These fibers may be natural or synthetic. Examples of natural fibers suitable for forming the storage layer include, for example, cellulose fibers, wood pulp fibers, regenerated cellulose, cotton fibers, hydroentangled fluff pulp, fluff pulp, tissue and the like. Synthetic fibers may, for example, be formed from absorbent materials or from one or more polyolefins.

In some instances, the product may be required to withstand multiple liquid insults or wettings before being replaced. As such, the designers and engineers of such products are constantly challenged to develop innovative combinations of materials which not only adequately manage surge, distribution and retention of liquids from an initial wetting, but which also adequately manage liquids from subsequent wettings. The designers' and engineers' tasks are made more formidable in view of the business and economic realities of producing such products for disposable markets. Therefore, there exists a need to manufacture such absorbent articles having improved liquid management capabilities.

Furthermore, some traditional absorbent article manufacturing practices have formed the storage layer from a combination of randomly distributed fibers and randomly distributed absorbent materials. In other words, for example, analysis of fiber and absorbent particle size samples taken across the storage layer would generally indicate that the distribution of large and small fibers and/or particles in these samples is generally uniform. Additionally, traditional absorbent article manufacturing practices have merely loosely combined the variously sized fibers and absorbent particles therein. By merely loosely combining the fibers and absorbent particles within the absorbent article, vibrations, such as shipping and handling induced vibrations, may induce fiber/absorbent particle segregation within the absorbent article. In some instances, such fiber/absorbent particle segregation may decrease the liquid management capabilities of the absorbent article.

SUMMARY OF THE INVENTION

In response to these traditional absorbent article manufacturing practices, the present invention provides for an absorbent article and methods of forming the same wherein the absorbent article includes a particle size gradient having a coarse zone and a fine zone. Particularly, the particle size gradient may extend along either the width dimension or the length dimension of the absorbent article and more particularly, the size gradient may extend along the length dimension of the absorbent article. The particles may be aqueous liquid absorbent materials.

The present invention further provides for an absorbent article and methods of forming the same wherein the absorbent article includes multiple-sized absorbent material and/or multiple-sized fibrous material and wherein at least one of the materials is present in the absorbent article in a size gradient. Particularly, the size gradient may be present in the width dimension or the length dimension of the absorbent article and more particularly, the size gradient may be present in the length dimension of the absorbent article. The particles may be aqueous liquid absorbent materials. The fibers may be natural fibers, synthetic fibers or a combination of natural and synthetic fibers. The size gradient in the absorbent article may include coarse and fine particle zones and/or coarse and fine fiber zones.

When the absorbent article is formed from multiple sized fibers and multiple sized absorbent particles, both the multiple sized fibers and multiple sized absorbent particles may be formed in size gradients In one embodiment, the coarse zone of fibers may be combined with the coarse zone of absorbent particles. Additionally, the fine zone of fibers may be combined with the fine zone of absorbent particles. In another embodiment, the coarse zone of the fibers may be combined with the fine zone of absorbent particles and the coarse zone of the absorbent particles may be combined with the fine zone of fibers.

The present invention further provides for an absorbent article and methods of forming the same wherein the absorbent article includes absorbent particles coupled to fibers. More particularly, the present invention provides for an absorbent article formed from absorbent particles which are electrostatically coupled to the fibers.

BRIEF DESCRIPTION OF THE DRAWINGS

FIG. 1 is a schematic front view of an electrostatic separator for manufacturing an article of the present invention.

FIG. 1A is an enlarged fragmented perspective view of a portion of the apparatus illustrated in FIG. 1.

FIG. 1B is another embodiment of a portion of the apparatus illustrated in FIG. 1.

FIG. 2 is a fragmented schematic cross sectional view of an absorbent article.

FIG. 2A is an illustration of a x, y and z axes grid.

DETAILED DESCRIPTION OF THE INVENTION

Figure 3:
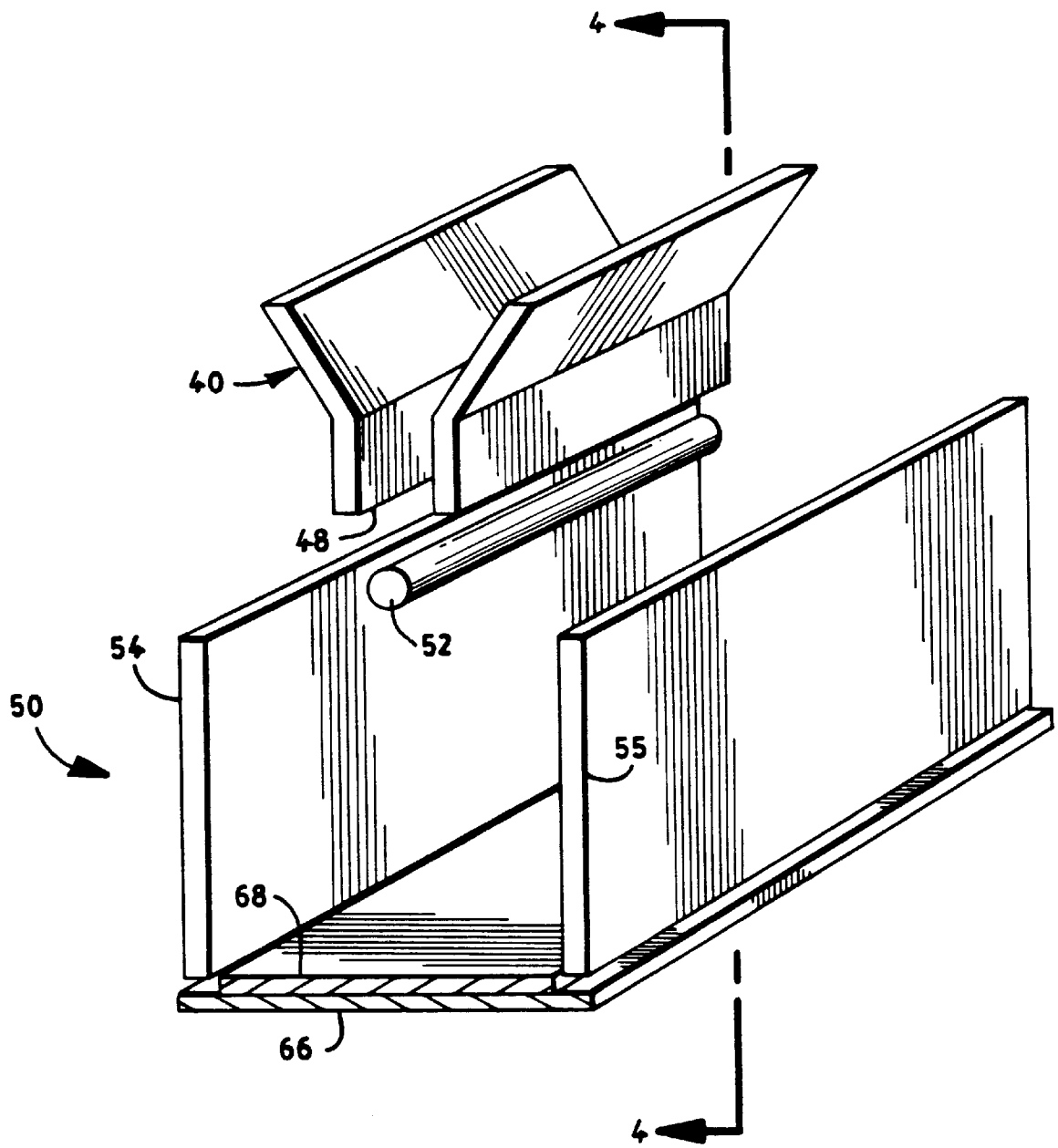
FIG. 3 is a perspective view of a portion of the apparatus illustrated in FIG. 1.

As used herein, the term "absorbent material" refers to a high-absorbency material and may further include "absorbent particles" or "fibrous absorbent materials". These high-absorbency materials are generally capable of absorbing an amount of a liquid, such as water, synthetic urine, a 0.9 weight percent aqueous saline solution, or other bodily liquids such as menses or blood, generally equal to at least 10, suitably about 20, and in some embodiments up to about 100 times the weight of the absorbent material being used. Typical conditions include, for example, a temperature of between about 0° C. to about 100° C. and suitably ambient conditions, such as about 23° C. and about 30 to about 60 percent relative humidity. Upon absorption of the liquid, the absorbent material typically swells and forms a gel.

The absorbent material may be formed from an organic material, which may include natural materials such as agar, pectin, and guar gum, as well as synthetic materials such as synthetic polymers. Synthetic hydrogel polymers include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyrridines. Other suitable polymers include hydrolyzed acrylonitrile-grafted starch, acrylic acid-grafted starch, and isobutylene maleic anhydride copolymers and mixtures thereof. The polymers are preferably lightly crosslinked to render the material substantially water insoluble yet water swellable. Crosslinking may, for example, be by irradiation or by covalent, ionic van der Waals, or hydrogen bonding Suitable absorbent materials are typically available from various commercial vendors, such as The Dow Chemical Company, Hoechst-Celanese, Allied Colloids Limited, or Stockhausen, Inc. For example, Dow 2054 is a polyacrylate absorbent material available form The Dow Chemical Company and IM 3900 is a polyacrylate absorbent material available form Hoechst-Celanese.

The absorbent material employed in the absorbent structures of the present invention suitably should be able to absorb a liquid under an applied load. For the purposes of this application, the ability of a absorbent material to absorb a liquid under an applied load and thereby perform work is quantified as the Absorbency Under Load (AUL) value. The AUL value may be expressed as the amount (in grams) of an aqueous 0.9 weight percent sodium chloride solution which the absorbent material can absorb per gram of absorbent material under a load of, for example, about 0.3 pounds per square inch (approximately 2.0 kilopascals) while restrained from swelling in the plane normal to the applied load. The absorbent material employed in the absorbent structures of the present invention generally exhibit an AUL value of at least about 15, more suitably of at least about 20, and up to about 50. The method by which the AUL value is determined is set forth in detail in U.S. Pat. Nos. 5,149,335 and 5,247,072 which are herein incorporated in their entirety by reference.

The absorbent material is generally in the form of particles which, in the unswollen state, generally have normal cross-sectional diameters within the range of from about 10 microns and to about 850 microns, as determined by sieve analysis using U.S. Standard Sieves manufactured according to ASTM Ell-81 specifications. It is understood that the particles of absorbent material falling within the ranges described above may comprise solid particles, porous particles, or may be agglomerated particles comprising many smaller particles agglomerated into particles falling within the described size ranges.

The absorbent material may also be in the form of fibers. Fibrous absorbent material may generally have a length of between about 0.1 cm to about 15 cm and a diameter of between about 0.2 microns to about 300 microns.

As used herein, the term "size gradient" means a gradient having at least one "coarse zone" and at least one "fine zone" The term "size gradient" may refer to particles and/or fibers. When the term "size gradient" refers to particles, the particle size gradient means a gradient having at least a coarse particle zone and at least a fine particle zone. The coarse and fine particle zones may abut each other or they may be separated by intermediate zones. Such intermediate zones may include substantially particle-free zones, non-coarse zones, non-fine zones, or randomly distributed particle zones.

A coarse particle zone may be defined as a zone wherein the percent by weight deficiency of small particles is greater than about 5%, and particularly greater than about 10%, and more particularly greater than about 15%, and still more particularly greater than about 20% of the otherwise random percent by weight distribution of such small particles within the sampled absorbent article. For the purpose of this definition, small particles may be considered to be particles of a smaller size as compared to other particles within the sampled absorbent article, or may be considered to be particles who's size falls within some small particle size range. The coarse particle zone may also be defined as a zone wherein the percent by weight surplus of large particles is greater than about 5%, and particularly greater than about 10%, and more particularly greater than about 15%, and still more particularly greater than about 20% of the otherwise random percent by weight distribution of such large particles within the sampled absorbent article. For the purpose of this definition, large particles may be considered to be particles of a larger size as compared to other particles within the sampled absorbent article, or may be considered to be particles who's size falls within some large particle size range.

A fine particle zone may be defined as a zone wherein the percent by weight deficiency of large particles is greater than about 5%, and particularly greater than about 10%, and more particularly greater than about 15%, and still more particularly greater than about 20% of the otherwise random percent by weight distribution of such large particles within the sampled absorbent article. For the purpose of this definition, large particles may be considered to be particles of a larger size as compared to other particles within the sampled absorbent article, or may be considered to be particles who's size falls within some large particle size range. The fine particle zone may also be defined as a zone wherein the percent by weight surplus of small particles is greater than about 5%, and particularly greater than about 10%, and more particularly greater than about 15%, and still more particularly greater than about 20% of the otherwise random percent by weight distribution of such small particles within the sampled absorbent article For the purpose of this definition, small particles may be considered to be particles of a smaller size as compared to other particles within the sampled absorbent article, or may be considered to be particles who's size falls within some small particle size range.

When the term "size gradient" refers to fibrous absorbent material, the size gradient means a gradient having at least a coarse fibrous absorbent material zone and a fine fibrous absorbent material zone. The coarse fibrous absorbent material zone is defined by a majority by weight of such fibers therein having a diameter greater than about 100 microns, for example, having a diameter between about 100 microns to about 250 microns, and such as having a diameter between about 100 microns to about 150 microns. The fine fibrous absorbent material zone is defined by a majority by weight of such fibers therein having a diameter less than about 100 microns, and for example having a diameter between about 10 microns to about 90 microns, and such as having a diameter between about 30 microns to about 70 microns.

When the term "size gradient" refers to other fibers, the fiber size gradient means a gradient having at least a coarse fiber zone and at least a fine fiber zone. The coarse fiber zone is defined by a majority of the fibers therein having a diameter greater than about 10 microns. More particularly, the coarse zone of fibers is defined by a majority of the fibers therein sized from between about 10 microns to about 30 microns in diameter The fine zone of fibers is defined by a majority of the fibers therein having a diameter less than about 10 microns and more particularly, the fine zone of fibers is defined by a majority of fibers therein having a diameter from between about 0.2 microns to about 5 microns.

When fibers are loosely distributed within the absorbent article, the length of such fibers is generally between about 0.1 cm to about 15 cm, and particularly from about 0.2 cm to about 7 cm. Loosely distributed fibers include fibrous absorbent material and natural fibers and synthetic fibers.

Generally, the orientation of a size gradient, particularly within an absorbent article, may be in either the x, y or z axis, i.e. the length, width or height dimension, respectively, or a combination thereof. Desirably, the size gradient orientation, particularly within an absorbent article, will be along the length of the absorbent article or x axis of the absorbent article.

Turning now to the drawings and referring first to FIG. 1, an electrostatic separator 20 is illustrated. The electrostatic separator 20 includes an particle bin 22 having an upper portion 24 defining an opening 26 for receiving the absorbent particles A lower portion 28 of the bin 22 converges and defines, in cross section, a generally V-shaped structure. A bottom portion 30 of the lower portion 28 is provided with a plurality of spaced apart openings 32 (FIG. 1A). A rotatable agitator 34 having a plurality of outwardly projecting agitator fins 36 is mounted within the bin 22 and above the bottom portion 30. A gate 38 is slidably mounted to the exterior of the bottom portion 30 of the bin 22. In this way, by selectively positioning the gate 38 with respect to the openings 32, the flow of absorbent particles exiting the bin 22 through the openings 32 may be controlled. The flow of absorbent particles can also be controlled by varying the speed of the agitator 34.

Below the bin 22 is an absorbent particle channeling structure 40. The channeling structure 40 is funnel-shaped. The upper portions 41 and 42 of the channeling structure 40 diverge upwardly and toward the bottom portion 30 of the bin 22 and define a receiving opening 44. The lower portions 45 and 46 of the channeling structure 40 define a discharge opening 48.

A gradient forming chamber 50 is generally positioned below the discharge opening 48 of the channeling structure 40. An electric field is formed within the gradient forming chamber 50 by an electric field initiating structure (hereinafter referred to as an "EFIS") to which a high voltage is applied. Spaced a distance from the EFIS is an electric field receiving structure (hereinafter referred to as an "EFRS") to which voltage may or may not be applied.

Referring to FIG. 1 for example, and not by way of limitation, such an EFIS may include a conductive wire 52. Suitable conductive materials for forming the wire 52 include, but are not limited to, copper, tungsten and stainless steel. The EFRS may for example include a pair of spaced apart conductive plates 54 and 55. Suitable conductive materials for forming the plates 54 and 55 include, but are not limited to aluminum, steel and stainless steel. In this way, for example, upon the application of sufficient voltage to the wire 52 and grounding the plates 54 and 55, ions are generated at the wire 52. The electric field formed within the gradient forming chamber 50 directs these ions to flow in a direction from the wire 52 (EFIS) toward the plates 54 and 55 (EFRS). This condition is generally referred to as "corona discharge".

With continued reference to FIG. 1, generally, in the operation of the electrostatic separator 20, a quantity of absorbent particles (not shown) is introduced, via the opening 26, into the bin 22. By selectively controlling the direction of rotation and the rotational speed of the agitator 34, the dimension and position of the fins 36, the size of the openings 32, and the position of the gate 38 with respect to the openings 32, a controlled stream of absorbent particles exits the bin 22.

The absorbent particle stream exiting the bin 22 enters the channeling structure 40 via opening 44. The absorbent particle stream is narrowed by the lower portions 45 and 46 of the channeling structure 40 such that a narrow absorbent particle stream exits the discharge opening 48. Alternately, the channeling structure 40 may include a divider 47, as illustrated in FIG. 1B. The divider 47 separates the channeling structure 40 into two chambers. Generally, the divider 47 extends from the receiving opening 44 to the discharge opening 48 of the channeling structure 40. In this way, the divider 47 may be used to segregate the absorbent particles entering the channeling structure 40 on one side of the divider 47 from the absorbent particles entering the channeling structure 40 on the other side of the divider 47. The divider 47 may also function to prevent the absorbent particles exiting the channeling structure 40 from striking the wire 52 and thereby prevents the particles from being deflected by impact with the wire 52.

The lower portions 45 and 46 of the channeling structure 40 have a dual function. First, as previously stated, the lower portions 45 and 46 train the absorbent particle stream entering the channeling structure 40 into a narrow particle stream. And second, the discharge opening 48 orients the narrowed particle stream exiting the channeling structure 40 relative to the gradient forming chamber 50. For example, but not by way of limitation, as illustrated in FIG. 1, the channeling structure 40 orients the narrowed particle stream parallel to and near the wire 52. As the narrowed particle stream moves vertically through the gradient forming chamber 50, the particles cross the path of the ions flowing from the wire 52 toward the plates 54 and 55. The particles become charged by intercepting a portion of these ions. Charging in this manner is generally referred to as "corona charging".

As the particles continue to travel through the gradient forming chamber 50, the now charged particles within the stream tend to move in a generally lateral direction toward either plate 54 or 55 due to the electric field between the wire 52 and the plates 54 and 55. The acceleration of each particle in the lateral direction towards the plates 54 or 55 is inversely proportional to the radius of the particle. Thus, assuming that the density of both the smaller and larger particles are relatively the same, the smaller particles accelerate more rapidly than the larger particles. In this way, the narrowed absorbent particle stream entering the gradient forming chamber 50 expands generally laterally as the stream travels through the gradient forming chamber 50. The particle distribution within the expanded stream is such that the larger particles occupy a more central location within the expanded stream and the smaller particles occupy a more peripheral or lateral location within the expanded stream. As such, generally the particle size distribution across the expanded particle stream or the transition, for example, from smaller particles to larger particles across the expanded particle stream is generally continuous.

As will be discussed in greater detail below, upon exiting the gradient forming chamber 50, the expanded stream of absorbent particles may be deposited on a support layer so as to form a size gradient of absorbent particles on the support layer. Additionally, the absorbent particles may be selectively directed or zoned, via discrete chambers, onto a support layer. In this way, a size gradient of absorbent particles may be formed on selected portions of the support layer.

As with the formation of the stream of absorbent particles exiting the bin 22, there are also a number of variables that affect the particle size distribution of absorbent particles within the gradient forming chamber 50 and ultimately the formation of the absorbent particle size gradient within the absorbent article. One such variable is the strength of the electric field. Higher voltages, of either positive or negative polarity, will produce stronger electric fields. Stronger electric fields will result in greater accelerative forces being exerted upon the charged particles which in turn will result in greater particle movement or particle deflection within the gradient forming chamber 50. Thus, by varying the strength of electric field, particle migration or particle deflection within the gradient forming chamber 50 may be varied and thus controlled.

One method of varying the electric field strength is to vary the voltage and polarity applied to the EFIS. Another method of varying the electric field strength is to vary the voltage and polarity applied to the EFRS. For example, referring again to FIG. 1, for a given voltage applied to the wire 52, if the plates 54 and 55 are isolated from earth ground and are charged to a polarity opposite to that applied to the wire 52, the electric field strength will increase proportionately to the voltage applied to the plates 54 and 55. Conversely, if a voltage having the same polarity as that on the wire 52 is applied to the plates 54 and 55, the electric field strength will decrease in proportion to the voltage applied to the plates 54 and 55. An application of this technique may be useful for varying the distribution of the size gradients formed on either side of the wire 52. Different size gradients may be formed by applying a different voltage to the plate 54 than to the plate 55. These voltages may differ in both polarity and magnitude.

Electric field strength is also dependent upon the physical distance between the EFIS and the EFRS. For a given applied voltage, the electric field strength is inversely proportional to the distance between these two structures.

For example, if the wire 52 represents the EFIS and the plates 54 and 55 represent the EFRS, the electric field strength can be increased by merely bringing the plates 54 and 55 closer to the wire 52, or decreased by moving the plates 54 and 55 further from the wire 52. As such, the dimension and/or distribution of the size gradients on either side of the wire may be varied by placing one of the plates, for example plate 55, at a different distance from the wire 52 than the other plate, for example plate 54.

With continued reference to the EFIS/EFRS model described in the previous paragraph, another variable which may affect the particle size distribution within the gradient forming chamber 50 is the diameter of the wire 52. Since the charge density on a conductor is inversely proportional to the radius of curvature, the diameter of the wire 52 will affect the onset of corona discharge from the wire 52. As such, the corona discharge may occur at a lower applied voltage for a smaller diameter wire which in turn may permit the particle stream to be charged at a reduced average electric field strength. In some instances, the deflection of the particle stream may be reduced. The reduction in particle deflection may be overcome by increasing the applied voltage to the wire 52, which in turn increases the average electric field strength. However, as the diameter of the wire 52 decreases, the wire's durability may be adversely affected.

Another variable which may affect the particle size distribution within the gradient forming chamber 50 is the conductivity of the dielectric medium therein. If, for example, the dielectric medium is air, the selected electric field strength may not be supportable within the gradient forming chamber 50 if the air's moisture content is sufficiently high. When the moisture content in the air is sufficiently high, the air will begin to conduct electricity. In this case, an electrical arc or spark may occur between the wire 52 and one or more of the plates 54 and 55.

The flow of absorbent particles into the gradient forming chamber 50 may also affect the resulting particle size gradient. As previously discussed, the particle size gradient is formed by the unique reaction/acceleration of each of the variously sized charged particles within the gradient forming chamber 50. However, there are at least two situations related to the manner in which the absorbent particles flow which may affect the formation of the size gradient. Both of these situations relate to the flow of the absorbent particles past the wire 52.

In the first situation, a large particle is positioned between a smaller particle and the wire 52. The resulting effect is that the larger particle shields the smaller particle from the flow of charging ions. Since the smaller particle is in the shadow of the larger particle and therefore does not intercept any or relatively few of the charging ions, the smaller particle does not become sufficiently charged. As a result, the degree to which the smaller particle is deflected within the gradient forming chamber 50 may be impaired.

In the second situation, the smaller particle is positioned between the larger particle and the wire 52. In this case, while the smaller particle is not shielded from the flow of charging ions and is thus able to be charged, its movement within the gradient forming chamber 50 may be impaired, such as by collision with the larger particle.

Both "shielding" and "collision" E effects between particles in the gradient forming chamber 50 can be reduced by narrowing the particle stream entering the forming chamber 50. While a monolayer particle stream would generally avoid these effects completely, in most commercial applications, such a narrow stream of particles would not be practical.

While narrowing the particle stream may avoid some of the effects of particle "shielding" and/or "collision", narrowing the particle stream may also reduce particle throughput. However, the reduction in particle throughput may be compensated for by increasing the length of the narrow particle stream so as to form a narrow curtain-like particle stream. A particle curtain stream may be formed by maintaining the width of the discharge opening 48 while increasing the overall length the electrostatic separator, particularly the length of the bin 22, the channeling structure 40 and the gradient forming chamber 50 as illustrated in FIG. 3.

Another method which may increase the particle throughput would be to increase the velocity of the particles flowing through the channeling structure 40 and past the wire 52. An example of one method for increasing the particle velocity within, for example, the gravity feed system illustrated in FIG. 1 would be to increase the distance between the receiving opening 44 of the channeling structure 40 and the bottom 30 of the bin 22. Another method of increasing the particle velocity would be by a forced gas induction means. In this case, the absorbent particles are metered into a stream of gas, such as air. The particle laden stream of air is directed into the channeling structure 40 for appropriate narrowing before passing into the gradient forming chamber 50. It will be understood that any turbulent gas movement within the electrostatic separator 20, and particularly within the chamber 50, may also affect the particle size distribution within the absorbent article. In each of these examples, since the absorbent particles are flowing faster through the gradient forming chamber 50, the design of the chamber may have to be modified to obtain the desired distribution. Such modifications may include extending the height of the gradient forming chamber 50 and/or increasing the strength of the electric field therein.

Another variable which may affect the particle size distribution within the gradient forming chamber 50 is the particle size distribution within the quantity of particles introduced into the bin 22. For example, where the quantity of particles in the bin 22 is made up of mostly large particles and only a few small particles, the mass distribution in the resulting particle gradient will not be uniform In other words, there will be a greater mass concentration in the coarse zone than in the fine zone.

Similarly, if the quantity of the particles in the bin 22 is made up of mostly small particles and only a few large particles, again, the particle mass distribution will not be uniform In this case, there will be a greater mass concentration in the fine zone than in the coarse zone.

If the absorbent material is concentrated in such mass predominate zones, the liquid management capabilities of the absorbent article may be diminished. If it is desirable to avoid the formation of such mass predominate zones within the absorbent article, the electric field strength may be varied. By varying the electric field strength, the mass predominate zones may be expanded. For example, if "large" is the predominate particle size within the quantity of particles, by increasing the electric field strength, the resulting coarse zone will be expanded or, if "small" is the predominate size within the quantity of particles, by decreasing the electric field strength, the resulting fine zone will be expanded. Additionally, the mixture of particles may be adjusted so that there is a predetermined amount of each particle size present in the bin 22.

Referring to FIG. 2, an absorbent structure 56 is schematically illustrated having a thickness dimension, a width dimension and a length dimension. The thickness dimension of the absorbent structure 56 is indicate by the z axis of FIG. 2A. The length dimension of the absorbent structure 56 is indicated by the x axis of FIG. 2A and the width dimension of the absorbent structure 56 is indicated by the y axis of FIG. 2A.

The absorbent structure 56 includes a plurality of functional zones, 58, 60, 62 and 64. Generally, each functional zone is in a juxtaposed and contacting relationship with adjacent functional zones. The first functional zone 58 may be porous and performs a liquid surge function. The second functional zone 60 may be porous and performs a liquid distribution function. The third functional zone 62 may be porous and performs a liquid storage function. The fourth functional zone 64 is desirably liquid impervious and performs a liquid barrier function. It is understood that while a plurality of layers may be combined into a single functional zone, or that a plurality of such functional zones may be combined into a single layer, for purposes of discussion, the absorbent structure 56 will be described herein as having separate layers for each functional zone.

Generally, the pore size of the first functional zone 58 may be larger than the pore size of the second functional zone 60. The first and second functional zones, 58 and 60 respectively, may be a nonwoven fabric formed from fibers. More particularly, said nonwoven fabric may be formed from fibers formed from one or more melt-extruded thermoplastic polymers.

By way of example only, thermoplastic polymers may include: end-capped polyacetals, such as poly (oxymethylene) or polyformaldehyde, poly (trichloroacetaldehyde), poly(n-valeraldehyde), poly (acetaldehyde), poly(propionaldehyde), and the like; acrylic polymers, such as poly(ethyl acrylate), poly(methyl methacrylate), and the like, fluorocarbon polymers, such as perfluorinated ethylene-propylene copolymers, ethylenetetrafluoroethylene copolymers, poly (chlorotrifluoroethylene), ethylene-chlorotrifluoroethylene copolymers, poly(vinylidene fluoride), poly(vinyl fluoride), and the like; polyamides, such as poly(6-aminocaproic acid) or poly(ε-caprolactam), poly(hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly (sulfonyl-1,4-phenyleneoxy-1,4-phenylenesulfonyl-4,4'-biphenylene), and the like; polycarbonates, such as poly (bisphenol A) or poly(carbonyldioxy-1,4-phenyleneisopropylidene-1,4-phenylene), and the like; polyesters, such as poly(ethylene terephthalate), poly (tetramethylene terephthalate), poly(cyclohexylene-1,4-dimethylene terephthalate) or poly(oxymethylene-1,4-cyclohexylenemethyleneoxyterephthaloyl), and the like; polyaryl sulfides, such as poly(p-phenylene sulfide) or poly (thio-1,4-phenylene), and the like; polyimides, such as poly (pyromellitimido-1,4-phenylene), and the like; polyolefins, such as polyethylene, polypropylene, poly(1-butene), poly (2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly (vinylidene chloride), polystyrene, and the like; copolymers of the foregoing, such as a polypropylene-ethylene, polypropylene-polyethylene, polyethylene-polyvinyl alcohol, acrylonitrile-butadienestyrene (ABS) copolymers, and the like.

The first functional zone 58 may be formed from a nonwoven fabric formed from melt-extruded thermoplastic polymer fibers having an average diameter of between about 10 microns to about 50 microns, and particularly between about 10 microns to about 30 microns and has a basis weight of at least about 0.25 ounces per square yard (osy) and a density of at least about 0.01 g/cc. More particularly, the basis weight and density may range from between about 0.25 to about 10.0 osy and about 0.01 to about 0.15 g/cc, respectively, and still more particularly from between about 0.5 to about 5 osy and about 0.01 to about 0.1 g/cc, respectively and still more particularly from between about 1.0 to about 3 osy and about 0.01 to about 0.08 g/cc, respectively. The fibers forming the first functional zone 58 may further include a hydrophilic external or internal additive. Alternatively, the first functional zone 58 may be formed from a porous thermoplastic film having a hydrophilic internal additive or a porous foam having a hydrophilic internal additive. Such hydrophilic additives are described in U.S. patent application Ser. No. 08/242,948, which is assigned to the Kimberly-Clark Corporation, the assignee of record for this U.S. Patent Application, which is herein incorporated by reference in its entirety.

Desirably, the first functional zone 58 is a nonwoven fabric which may be formed by a variety of processes including, but not limited to, air laying processes, wet laid processes, hydroentangling processes, spunbonding, meltblowing, staple fiber carding and bonding, and solution spinning. It has been found that nonwovens formed from polyolefin-based fibers are particularly well-suited for the above applications. In one embodiment, the fibers of the first functional zone 58 are formed by spunbonding such that the resulting fibers are substantially continuous.

There are several types of polymer fibers useful for forming the first functional zone 58. Such fibers may be homo-polymeric, co-polymeric, bi-or multi-component polymeric or a blend of polymers. Polymers particularly well suited for forming such fibers include, for example, polyolefins, polyesters, such as PET, PVT and PBT, rayon, and polyamides such as nylons. More particularly, examples of suitable polyolefins include polypropylene, polyethylene, and polymer combinations such as polypropylene/ polyethylene, polypropylene/ethylene and polypropylene/ polybutylene.

When the first functional zone 58 is a porous film, said porous film may be formed by any one of several porous film forming processes known to those skilled in the art. When the first functional zone 58 is a porous foam, said porous foam may be formed by any one of several foam forming processes known to those skilled in the art.

The second functional zone 60 may be formed such that the surface energy and/or pore size of the second functional zone 60 differs from the first functional zone 58. Generally, it is desirable that the pore size and/or the surface energy of the first functional zone 58 be greater than the pore size and/or the surface energy of the second functional zone 60. In this way, the second functional zone 60 may receive and distribute the aqueous liquid from the first functional zone 58.

The second functional zone 60 may also be formed from the melt-extruded thermoplastic fibers described for forming the fibers of the first functional zone 58. More particularly, the second functional zone 60 may be a nonwoven fabric or web formed from melt-extruded thermoplastic fibers which are formed by meltblowing. The fibers of the second functional zone 60 may have a basis weight of at least about 0.25 osy and a density of at least about 0.01 g/cc. More particularly, the basis weight and density may range from between about 0.25 to about 10.0 osy and about 0.01 to about 0.15 g/cc, respectively, and still more particularly from between about 0.05 to about 5 osy and about 0.01 to about 0.1 g/cc, respectively and still more particularly from between about 1.0 to about 3 osy and about 0.01 to about 0.08 g/cc, respectively.

In some embodiments, the thermoplastic fibers forming the second functional zone 60 may have an average diameter range from between about 0.2 to about 10 microns. The fibers forming the second functional zone 60 may also be formed from natural fibers, such as for example, cellulose fibers, wood pulp fibers, regenerated cellulose, cotton fibers, hydroentangled fluff pulp, fluff pulp, tissue and the like.

Additionally, fibers forming the second functional zone may also be formed from a combination of synthetic fibers and natural fibers.

Additionally, the thermoplastic fibers forming the second functional zone 60 may also be bi- or multi-component fibers. Bi- or multi-component thermoplastic fibers and methods of making the same are disclosed in U.S. Pat. Nos. 5,238,733, 5,232,770, 4,547,420, 4,729,371, and 4,795,668, all of which are assigned to Minnesota Mining and Manufacturing Company and are herein incorporated by reference.

The third functional zone 62 may be formed from loose natural and/or synthetic fibers in combination with absorbent material. In the case of the present invention, a portion of the absorbent material, either absorbent particles and/or fibrous absorbent material, may be arranged in at least one size gradient within the third functional zone 62. Fibers suitable for use in the third functional zone 62 include cellulose fibers, hydrophilic-treated melt-extruded fibers, wood pulp fibers, regenerated cellulose, cotton fibers, or mixtures thereof. In many instances, the desired materials used in the third functional zone 62 of many absorbent articles are wood pulp fluff and hydrophilic-treated melt-extruded fibers. An important function of the third functional zone 62 is to provide liquid storage capacity for the absorbent article 56.

In operation, liquid contacting the first functional zone 58 of the absorbent article 56 quickly enters the first functional zone 58 and is urged toward the second functional zone 60. Within the second functional zone 60, the liquid is distributed and urged toward the third functional zone 62. Desirably, the liquid flow characteristics of the absorbent article 56 are such that liquid at the interface between zones 60 and 62 becomes absorbed and retained within the third functional zone 62. The fourth functional zone 64 prevents any liquid from leaking out of the absorbent article.

In addition to exposing the absorbent particles to electrostatic charging, other portions of the absorbent article, such as loose fibers, fiber webs, foams, and films, may also be electrostatically charged. For example, the absorbent particles may be coupled to loose fibers or a web if the polarity of the charge on the fibers or web is opposite to the polarity of the charge on the absorbent particles. In another case, the loose fibers or web may be charged such that the fibers or web repel the absorbent particles. In the first case, coupling the absorbent particles to the fibers and/or web may not only improve liquid distribution and uptake but may also reduce vibration induced absorbent particle segregation within the absorbent article. Such vibrational sources include shipping and handling vibration.

There are many techniques for charging fibers and webs. The fibers and webs may be charged by any suitable charging process known to those skilled in the art. For example, corona charging processes, such as the corona charging process employed in the gradient forming chambers described herein, may be used to charge fibers and webs. Another technique for charging webs is disclosed in U.S. patent application Ser. No. 07/958,958 filed Oct. 9, 1992 which is assigned to the University of Tennessee, and is herein incorporated in its entirety by reference.

Figure 4:
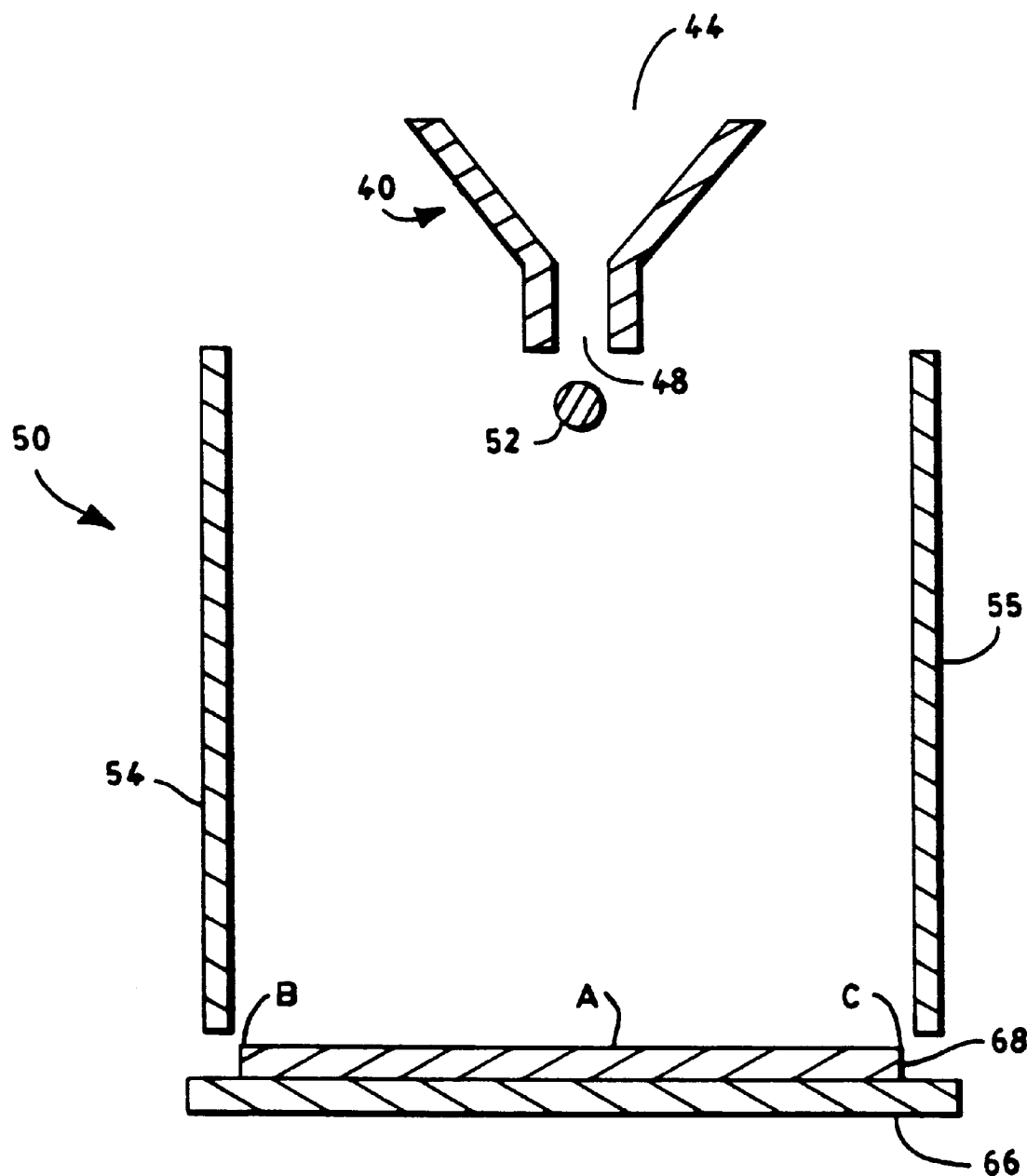
FIG. 4 is a cross sectional view of the apparatus illustrated in FIG. 3 taken along lines 4—4.

Referring now to FIGS. 3 and 4, portions of the electrostatic separator 20 have been removed and other portions enlarged for clarity of illustration. Additionally, the gradient forming chamber 50 is now positioned above a continuous belt or forming wire 66. Between the plates 54 and 55 and above the continuous belt 66 is a support layer 68. The support layer 68 is generally piloted between the plates 54 and 55 by the continuous belt 66. In this way, absorbent particles exiting the gradient forming chamber 50 are received and supported on the support layer 68.

In one embodiment, the support layer 68 may form part of the absorbent article 56. For instance, the support layer 68 may be a liquid impervious layer, such as a film, which is incorporated into the fourth functional zone 64 of the absorbent article 56. In another embodiment, the support layer 68 may be a fibrous layer which, upon combination with the absorbent particles, forms a portion of the third functional zone 62. In another embodiment, the support layer 68 may be formed from tissue. Or, in yet another embodiment, the support layer 68 may form part of the continuous belt 66. The absorbent particles may be further conveyed via the support layer 68 to another location for combination with another part of the absorbent article, such as, for example, loose fibrous materials.

Referring now to FIG. 4, as previously discussed, upon the application of sufficient voltage to the wire 52, an electric field is formed within the gradient forming chamber 50. As the particles within an absorbent particle stream exit the discharge opening 48 of the channeling structure 40 and travel through the gradient forming chamber 50, the particles are deflected toward either the plate 54 or the plate 55. The smaller particles within the particle stream are accelerated toward either the plate 54 or the plate 55 more rapidly than the larger particles. As the particle stream expands and contacts the support layer 68, a fine-to-coarse particle size gradient is formed thereon in a direction from point B to point A, and a coarse-to-fine particle size gradient is formed thereon in a direction from the point A to point C. It should also be noted that the strength of the electric field generated within the gradient forming chamber 50 is not uniform. In the instance where a sufficiently high voltage is applied to the wire 52, the electric field strength within the gradient forming chamber 50 is strongest near the wire 52 and weakest near the plates 54 and 55.

Figure 5:
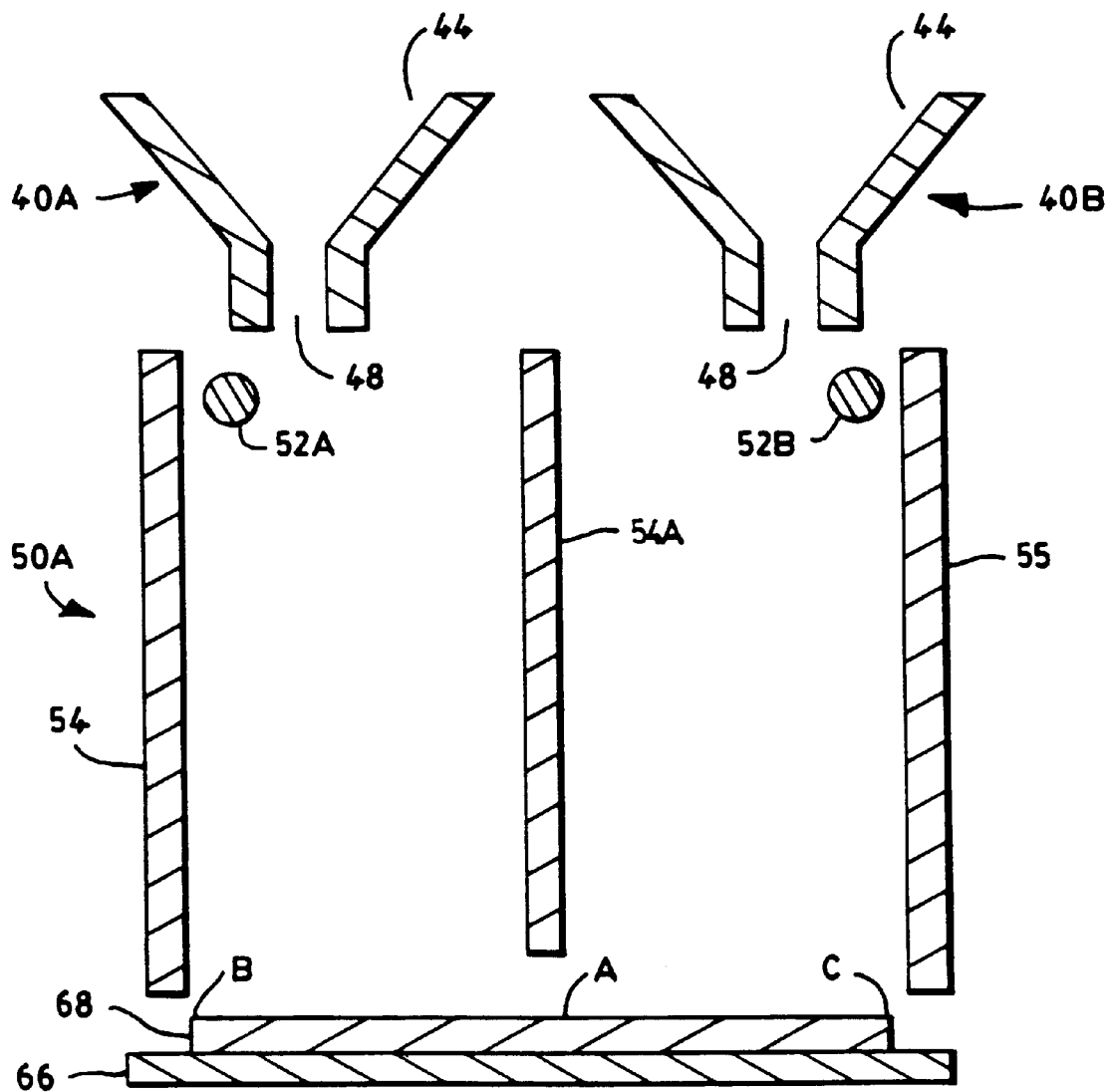
FIG. 5 is a cross sectional view of another embodiment of an apparatus for manufacturing an article of the present invention.

Referring now to FIG. 5, a forming chamber 50A is illustrated. The forming chamber 50A includes the pair of spaced apart plates 54 and 55 and a plate 54A positioned therebetween and generally above the center point A of the support layer 68. Located within the forming chamber 50A and positioned near the upper end of the plate 54 is a wire 52A and near the upper end of the plate 55 is a wire 52B. Positioned above each wire, 52A and 52B, and between each said wire 52A and 52B and the plate 54A is a channeling structure, either 40A or 40B. Each channeling structure, 40A and 40B, is provided with a receiving opening 44 and a discharge opening 48. The support layer 68 and the forming wire 66 are positioned at the base of the forming chamber 50A, generally below the plates 54, 55 and 54A.

Upon the application of sufficient voltage to the forming chamber 50A, a pair of electric fields may be formed when the EFIS includes the wires 52A and 52B and plates 54 and 55 and the EFRS includes the plate 54A. In this instance, upon the absorbent particle stream exiting the channeling structure 40A and traversing the gradient forming chamber 50A, a coarse-to-fine particle gradient would be formed in a direction from the point B toward the point A on the support layer 68. Furthermore, in addition to the gradient structure formed by an absorbent particle stream exiting the channeling structure 40A, an absorbent particle stream exiting the channeling structure 40B would form a coarse-to-fine particle gradient in a direction from the point C towards the point A.

It should be further noted that one of the factors which affects the amount of particulate material deposited on and supported by the support layer 68 directly beneath the plate 54A is the dimension of the plate 54A, and particularly the thickness of the bottom portion of the plate 54A. For example, if the bottom portion of the plate 54A was sufficiently flared or widened (not shown), the above described coarse-to-fine gradients formed on the support layer 68 would be separated by a substantially absorbent particle-free zone. The absorbent particle-free zone would generally be located around point A and below the bottom of the plate 54A.

Figure 6:
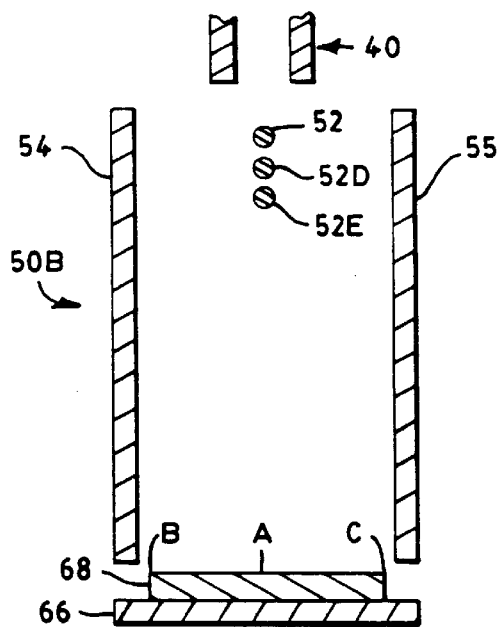
FIG. 6 is a cross sectional view of another embodiment of an apparatus for manufacturing an article of the present invention.

Referring now to FIG. 6, the gradient forming chamber 50B is similar to the gradient forming chamber 50 illustrated in FIG. 4 except that the chamber 50B includes wires 52D and 52E. By applying a voltage of the same polarity to the wire 52 and to one or both of the wires 52D and 52E, the EFIS extends further downward into the chamber 50B than the EFIS consisting of the single wire 52 (FIG. 4). As such, absorbent particles flowing past the wires 52, 52D and 52E traverse multiple electric fields and are thus charged and deflected multiple times. The effect of multiply charging the descending absorbent particles would be to deflect more of the larger particles toward points B and C on the support layer 68. It will be understood that one may vary the distance between the wires, the number of wires and the voltage applied to each wire to achieve a particular desired result.

Figure 7:
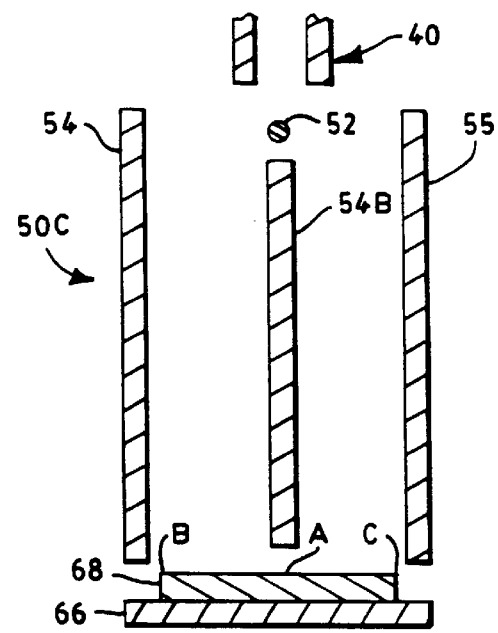
FIG. 7 is a cross sectional view of another embodiment of an apparatus for manufacturing an article of the present invention.

Turning now to FIG. 7, a gradient forming chamber 50C is illustrated which is similar to the forming chamber 50B except that the wires 52D and 52E are removed and replaced by a conductive plate 54B which is positioned below the wire 52. In the instance where the distance between the wire 52 and the plate 54B is sufficiently small, and a sufficiently high voltage is applied to the wire 52 an electric potential may be induced on the plate 54B. As such, descending charged absorbent particles would not only be deflected by the electric field formed by the wire 52 but also by the electric field formed by the plate 54B. In some instances, the gradient forming chamber 50C may provide a particle size gradient having a more uniform and thus more desirable particle size distribution than the particle size gradient formed by the gradient forming chamber 50 or 50B (FIGS. 4 and 6, respectively). The difference in the particle size gradients may result from the formation of a more uniform electric field between the EFIS and the EFRS within the chamber 50C as compared to the electric field within the chambers 50 and 50B.

Furthermore, depending upon the dimensions of the plate 54B, and particularly the thickness of the bottom portion of the plate 54B, a substantially absorbent particle-free zone may be formed along a portion of the support layer 68. For example, when the EFIS includes the wire 52 and the plate 54B and the EFRS includes the plates 54 and 55, an absorbent particle stream traversing the gradient forming chamber 50C and depositing on the support layer 68 would form a first fine-to-coarse size gradient in a direction from point B to the plate 54B and a second fine-to-coarse size gradient in a direction from point C to the plate 54B. Between these first and second size gradients and located generally around the point A would be a substantially absorbent particle-free zone.

Figure 8:
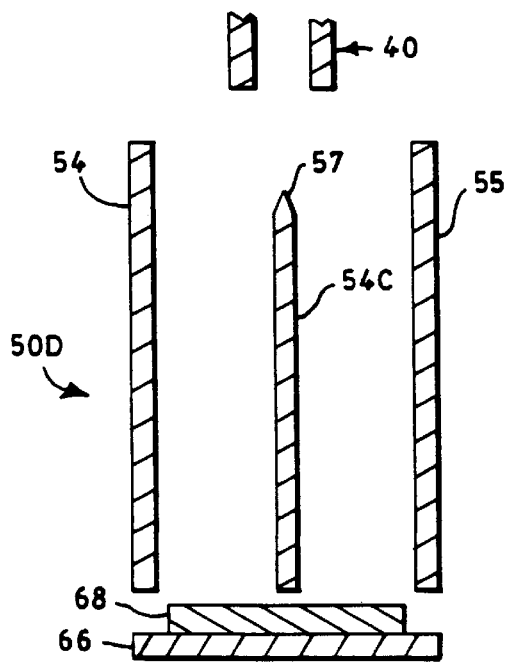
FIG. 8 is a cross sectional view of another embodiment of an apparatus for manufacturing an article of the present invention.

Referring now to FIG. 8, a gradient forming chamber 50D is illustrated The gradient forming chamber 50D is substantially similar to the gradient forming chamber 50C (FIG. 7) with the exception that the wire 52 and the plate 54B are replaced by a conductive plate 54C. The plate 54C is provided with an upper, pointed edge 57. As previously discussed with reference to FIG. 1, while the radius of curvature of the wire 52 may affect the corona discharge and the electric field within the gradient forming chamber 50, so too will the radius of curvature of the pointed edge 57 of the plate 54C affect the corona discharge and the electric field within the gradient forming chamber 50D. The absorbent particle size gradients formed by the chamber 50C may also be formed by the chamber 50D. The possible advantages of the singular design of the plate 54C over the free standing wire 52 and plate 54B combination illustrated in FIG. 7 include durability, electric field uniformity and ease of maintenance and adjustment within the chamber 50D.

Figure 9:
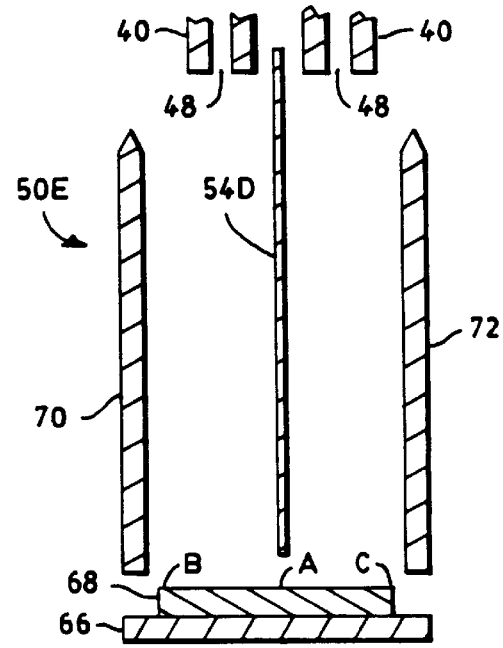
FIG. 9 is a cross sectional view of another embodiment of an apparatus for manufacturing an article of the present invention.

Referring now to FIG. 9, a gradient forming chamber 50E is illustrated The EFIS of the gradient forming chamber 50E is a pair of plates 70 and 72. The EFRS includes plate 54D which is positioned between the plates 70 and 72. The discharge opening 48 of a channeling structure 40 is position adjacent the upper edge of each of the plates 70 and 72. Upon the application of sufficiently high voltage to the plates 70 and 72, first and second electric fields are formed within the gradient forming chamber 50E. In this instance, as the absorbent particle streams traverse the length of the gradient forming chamber 50E and become charged and deflected, a coarse-to-fine-to-coarse size gradient is formed. One of the coarse zones begins near the edge of the support layer 68 which is indicated by point B and the other coarse zone begins near the edge of the support layer 68 which is indicated by point C. The fine zone is generally located about the center region of the support layer, indicated by the point A and between the coarse zones.

Figure 10:
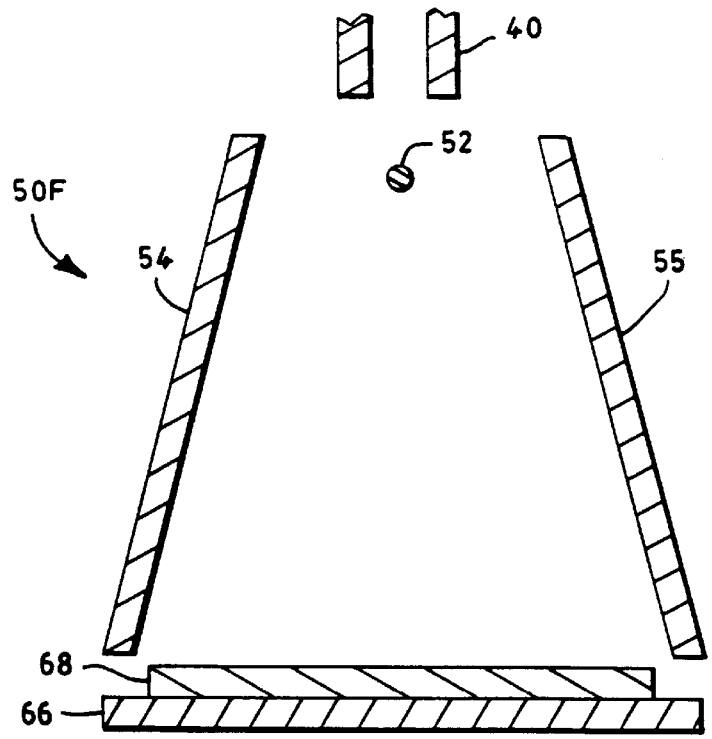
FIG. 10 is a cross sectional view of another embodiment of an apparatus for manufacturing an article of the present invention.

Referring now to FIG. 10, a gradient forming chamber 50F is illustrated The gradient forming chamber 50F is similar to the gradient forming chamber 50 (FIG. 4) except as to the orientation of the plates 54 and 55. In this instance, the tops of the plates 54 and 55 are angled towards or converge toward each other and the bottoms of the plates 54 and 55 are angled away from or diverge from each other. Assuming that the distance between the bottom of the plates 54 and 55 illustrated in FIGS. 10 and 4 are similar, by angling the tops of the plates 54 and 55 toward the wire 52, the distance between the tops of the plates 54 and 55 and the wire 52 within the chamber 50F (FIG. 10) is less than the distance between the tops of the plates 54 and 55 and the wire 52 within the chamber 50 (FIG. 4). In this way, an electric field of sufficient strength to form a particle size gradient may be generated at lower applied voltages on the wire 52 of the chamber 50F than on the wire 52 of the chamber 50.

Figure 11:
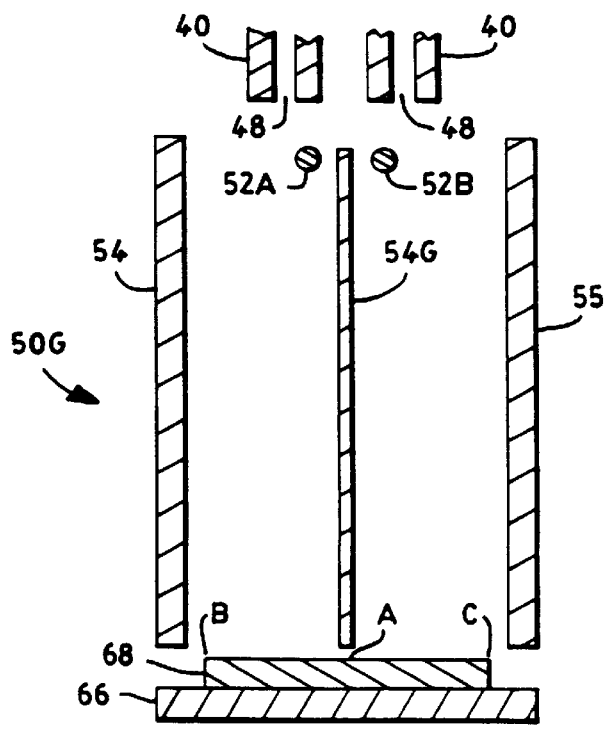
FIG. 11 is a cross sectional view of another embodiment of an apparatus for manufacturing an article of the present invention.

FIG. 11 illustrates a gradient forming chamber 50G for forming a fine-to-coarse and a coarse-to-fine particle size gradients on the support layer 68 with substantially no particles between the respective coarse zones. In this instance, the EFIS includes the wires 52A and 52B and plate 54G and the EFRS includes the plates 54 and 55.

A pair of channeling structures 40 are positioned above the chamber 50G. One of the discharge openings 48 of one of the channeling structures 40 is positioned such that a particle stream (not shown) exiting therefrom passes between the wire 52A and the plate 54. The other discharge opening 48 of the other channeling structure 40 is positioned such that a particle stream (not shown) exiting therefrom passes between the wire 52B and the plate 55. In this way, upon the application of sufficient voltage to the wires 52A and 52B, the fine particle zones generally extend inwardly from the respective edges of the support layer 68 (points B and C) and the coarse particle zones extend outwardly from either side of the center (point A) of the support layer 68. Additionally, voltage may also be applied to or induced on the plate 54G.

Figure 12:
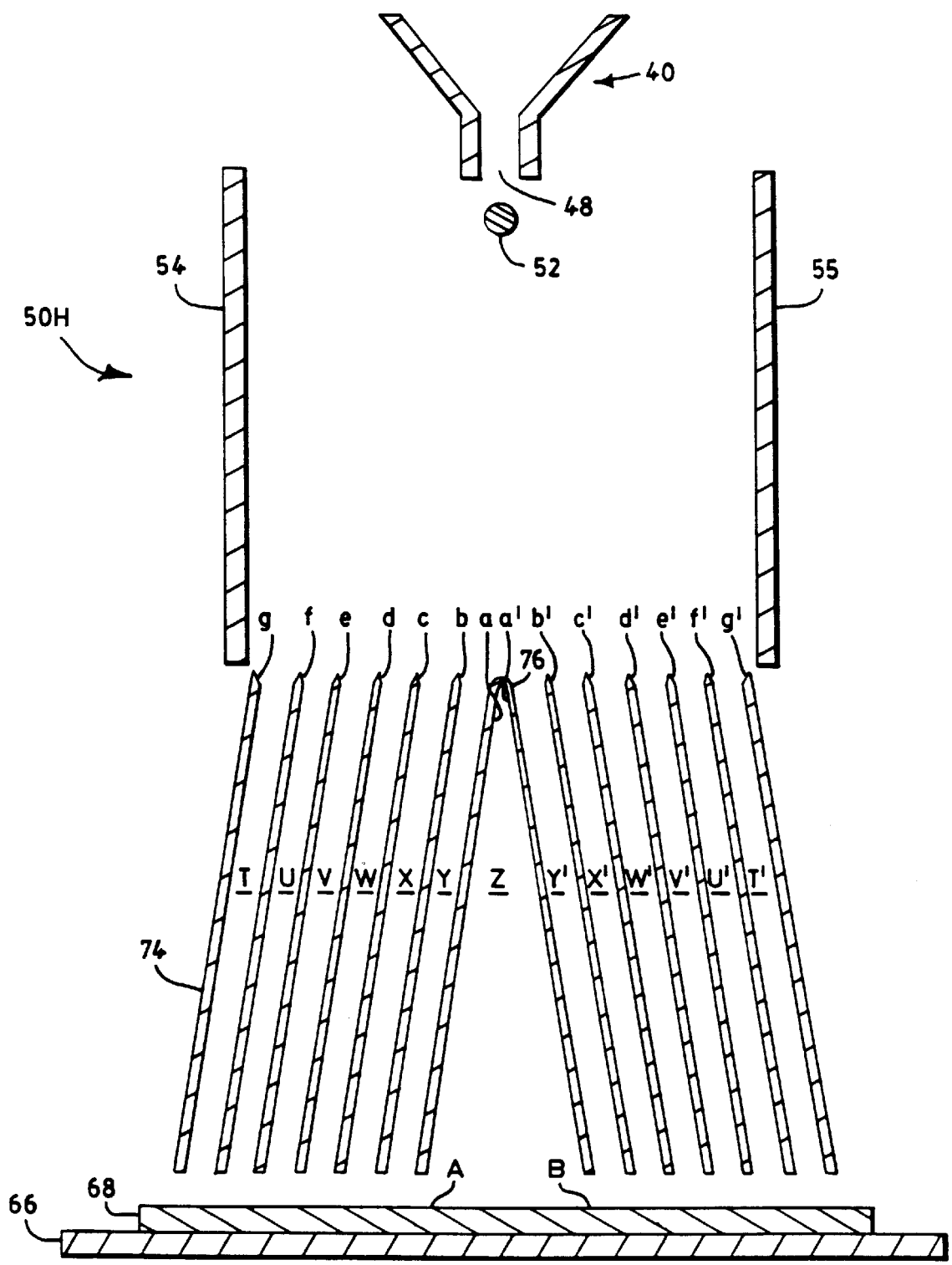
FIG. 12 is a cross sectional view of another embodiment of an apparatus for manufacturing an article of the present invention.

FIG. 12 illustrates a gradient forming chamber 50H which is substantially similar to the gradient forming chamber 50 illustrated in FIG. 4 except that a baffled structure 74 is positioned between the bottom of the chamber 50H and the support layer 68. The baffled structure 74 includes a plurality of through-conduits, i.e., T, T', U, U', V, V', W, W', X, X', Y, and Y' which are defined by the respective wall pairs g-f, f'-g', f-e, e'-f', e-d, d'-e', d-c, c'-d', c-b, b'-c', b-a and a'-b'.

A cavity Z, defined by the wall pair a-a' is closed to the forming chamber by an obstructive structure, such as a cap 76. In this way, particles traversing the chamber 50H are prevented from entering the cavity Z and thus generally do not become deposited between points A and B on the support layer 68. It will be understood that the obstructive structure 76 may be formed such that it may be removed so that particles may enter the cavity Z and be deposited on the support layer 68 between points A and B. Additionally, it will be understood that particle traversal through one or more of the conduits T through Y and T' through Y' may be prevented by positioning one or more similar obstructive structures at the top of and between the defining walls of such conduits. In this way, particle free zones, and particularly particle free zones between particle zones, may be formed along selected regions of the support layer 68.

Assuming for the moment that the obstructive structure 76 is removed, the baffled structure 74 may be positioned between the chamber 50H and the support layer 68 when it is desired to expand the particle coverage on the support layer 68 without adjusting the distance between the plates 54 and 55. It will be understood that while the baffled structure 74 expands the particle coverage, employing a structure between a gradient forming chamber and a support layer to decrease the particle coverage on the support layer without adjusting the distance between the plates 54 and 55 is now made clear to one skilled in the art. That is, the baffles can be angled inwardly as opposed to outwardly as is shown.

It will be understood that while the tops of the walls a-g and a'-g' are illustrated as generally equally spaced, varying the distance between the tops of such walls with respect to each other will affect the distribution of absorbent particles on the support layer 68.

Figure 13A:
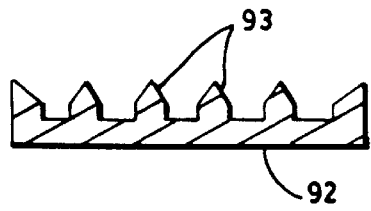
FIG. 13A is a cross sectional view of the structure illustrated in FIG. 13 taken along lines 13A—13A.
Figure 13:
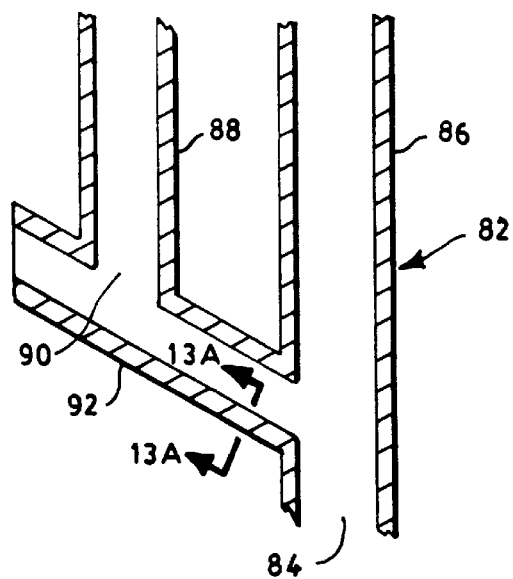
FIG. 13 is a schematic cross sectional side view of an apparatus for combining absorbent material with fibrous material.
Figure 14:
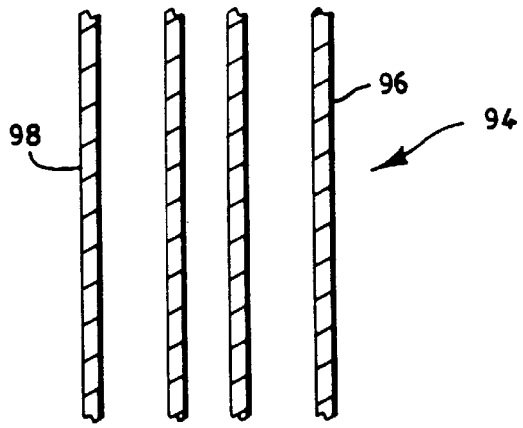
FIG. 14 is a schematic cross sectional side view of another embodiment of the apparatus illustrated in FIG. 13.

FIGS. 13 and 14 illustrate two embodiments for combining particulate material formed in size gradients according to the above described methods with the above described fibrous materials The two embodiments function similarly except that, as will be described in greater detail below, the fibers and the absorbent particles are combined prior to deposition on the forming wire by the embodiment illustrated in FIG. 13 and are separately deposited on the forming wire by the embodiment illustrated in FIG. 14.

Referring now to FIG. 13, a forming wire/support layer 78 is positioned between an optional vacuum source 80 and a dual-feed-single-discharge structure 82. The dual-feed-single-discharge structure 82 includes a discharge opening 84, a first feed conduit 86 in communication with the discharge opening 84, and a second feed conduit 88 having a discharge opening 90. The discharge opening 90 of the second feed conduit 88 communicates with the first feed conduit 86 via a connector conduit 92.

Within the second feed conduit 88 is positioned a gradient forming chamber (not shown) and particularly a gradient forming chamber having a baffled structure, and particularly a baffled structure generally similar to the embodiment described with reference to FIG. 12. Positioned within the connector conduit 92 and generally extending the length of the connector conduit 92, are particle dividers 93 (FIG. 13A), and particularly particle dividers which align with the walls of the baffled structure. One of the functions of the particle dividers is to assist in preserving the particle distribution formed in the second feed conduit by the gradient forming chamber as the expanded particle stream contacts the interior lower surface of the connector conduit 92. The dividers 93 may also be used, in a manner similar to the through conduits of the baffled structure 74, to separate, expand or contract the width of the particle stream and/or individual particle zones exiting the second feed conduit 88.

In operation, fibrous materials traversing the length of the first feed conduit 86 are combined therein with a size gradient-ordered particle stream exiting the connector conduit 92. The mixture of fibrous material and the size gradient-ordered particles is deposited on the forming wire/support layer 78. If it is desired to vacuum urge the fibrous material/particle mixture against the forming wire/support layer 78, the forming wire/support layer 78 should be sufficiently porous to permit a sufficient amount of air flow through the mixture without removing significant amounts of such mixture.

As previously discussed, the fibrous materials may be charged, and more particularly, may be charged with a polarity opposite to the polarity of the absorbent particles. If charging the fibrous materials is desired, the fibrous materials may be charged prior to being introduced into the first feed conduit 86. Alternatively, the fibrous materials may be charged with the desired polarity within the first feed conduit 86 by positioning a charging means, such as a corona discharge source, within the first feed conduit 86 and generally above the discharge opening of the connector conduit 92.

Referring now to FIG. 14, the forming wire/support layer 78 is positioned between the optional vacuum source 80 and a dual-feed-dual-discharge structure 94. The dual-feed-dual-discharge structure 94 includes first and second feed conduits, 96 and 98, respectively. The first and second feed conduits, 96 and 98, respectively, are similar to the first and second feed conduits 86 and 88 except that particles traversing the conduit 98 are deposited directly onto the forming wire/support layer 78 and are not communicated, via a connecting conduit, into the conduit 96. As such, with the exception of the connector conduit 92, generally, the structures employed and the various embodiments obtainable with respect to FIG. 13 may also be similarly employed and obtained with respect to the structures illustrated in FIG. 14.

With respect to FIG. 14, the fibers may be charge prior to being combined with the absorbent particles. Still more particularly the charging means may be positioned within the conduit 96 above and generally near the discharge open thereof.

In addition to forming absorbent particle size gradients within the absorbent article, the fibers, and particularly the fibers which are combined with the absorbent particles, may also be formed into fiber size gradients having coarse and fine zones. Fiber size gradients may be formed within the absorbent article by, for example, melt extruding then cutting to length one group of synthetic fibers which fall within the size range of the above describe fine fiber zone and melt extruding then cutting another group of synthetic fibers which fall within the size range of the above described coarse fiber zone. The individual groups of fibers may then be metered onto the forming wire or into a feed conduit, such as feed conduit 86 (FIG. 13) or feed conduit 96 (FIG. 14) and then ultimately onto the forming wire. In this way, the coarse and fine fiber size gradients may be selectively positioned within the absorbent article. Furthermore, multiple combinations of coarse and fine fiber size gradients in combination with coarse and fine absorbent particle size gradients may also be formed within the absorbent article.

As previously described, the absorbent particles in an unswollen state have a wide range of normal cross-sectional diameters, i.e. generally from about 10 to about 850 microns. During the manufacturing process of an absorbent article which includes such absorbent particles, controlling the emission of air-born absorbent particles is a concern. Of particular concern are air-born particles having a cross-sectional diameter of about 10 microns or less and particularly having a cross-sectional diameter of between about 10 microns to about 1 micron. Therefore, preventing or reducing the quantity of absorbent particles becoming air-born and particularly preventing or reducing the quantity of absorbent particles having cross-sectional diameters of 10 microns or less from becoming air-born is desirable.

It has been observed, upon the application of sufficient voltage to, for example, the gradient forming chamber 50 (FIG. 4) followed by the introduction therein of a stream of absorbent particles, that generally a portion of the smallest absorbent particles (cross-sectional diameters of from about 1 micron to about 100 microns) within the stream contacted and remained fixed to the EFRS. Furthermore, after a period of time, the particles adhering to the EFRS began to build up or "cake" thereon.

To remove the adhering particles from the gradient forming chamber, while at the same time minimizing the introduction of such particles into the air, the EFRS could be formed from a moveable conductive structure (not shown), more particularly a continuous conductive belt, and still more particularly a continuous conductive web. The continuous conductive web, supported by rollers, would generally circulate in and out of the gradient forming chamber. In this way, the portion of the conductive web within the gradient forming chamber to which the absorbent particles are adhering may be cycled outside the chamber while another portion of the conductive web, substantially free of adhering particles, would be entering the gradient forming chamber. Once outside the chamber, the adhering particles may be removed, such as by rinsing, brushing vacuuming, vibrating or any combination thereof.

The present invention is further described by the example which follows. Such example, however, is not to be construed as limiting in any way either the spirit or the scope of the present invention. In the example, all parts are by weight, unless stated otherwise.

EXAMPLE 1

Particle Size Gradient Formation

Absorbent particle size gradients were formed by using a gradient forming chamber similar to the gradient forming chamber 50 illustrated in FIG. 4. More particularly, the gradient forming chamber 50 was 17 inches wide by 3 inches in length and 17 inches in height. The receiving opening 44 of the dual chambered channeling structure 40 (FIG. 1B) was 17 inches above the wire 52. The wire 52 was formed from stainless steel, had a diameter of 0.020 inches and spanned the 3 inch length of the forming chamber. The dimension of each of the discharge openings 48 was 1/16 inch wide by 3 inches in length and was approximately ½ inch above the wire 52.

At the bottom of the gradient forming chamber 50 was positioned a 9 slot sample tray. With the exception of two slots, slots 1 and 9, located the respective ends of the sample tray, each of the intermediate slots, slots 2–8, was 2 inches wide. The slots 1 and 9 were 2.5 inches wide. The wire 52 was energized by 60,000 volts from a Glassman 60 KV/5 mA (300 W) regulated DC power supply.

The absorbent particle sample used in EXAMPLE 1 was prepared by sieving a quantity (greater than 100 Kg) of FAVOR 870 absorbent particles. FAVOR 870 absorbent particles are polyacrylate absorbent particles which are manufactured by Stockhausen. These absorbent particles were sieved into five fractions: greater than 630 microns, 630 microns to 420 microns, 420 microns to 310 microns, 310 microns to 177 microns and less than 177 microns. Equal amounts by weight of each fraction were then recombined. A 768 gram portion of this recombined mixture was run through the gradient forming chamber and collected in the 9 slot sample tray.

After capture of the 768 gram absorbent particle sample in the sample tray, the absorbent particles collected in each of the 9 slots were separately sieved to determine the fraction of particles within the below described size ranges. The absorbent particle sizes were grouped into five size ranges using U.S. Standard Sieves (ASTM E11-81 specifications) These size ranges were: Extra Large (XL)— greater than 600 microns, Large (L)—600 microns to 425 microns, Medium (M)—425 microns to 300 microns, Small (S)—300 microns to 180 microns and Extra Small (XS)— 180 microns to 75 microns. The percent by weight of the 768 gram absorbent particle sample in each of the above ranges was: XL—19.6%, L—16.4%, M—17.8%, S—21.9% and XS—22.3% Particles having a size of less than 75 microns accounted for about 2.1% by weight of the absorbent particle sample and as such, are not graphically illustrated in either FIGS. 15 or 16.

The data was analyzed by two methods. In the first method, the distribution of particles within the above defined size ranges in each slot was determined. This data is provided in TABLE I and illustrated graphically in FIG. 15. In the second method of data analysis, the distribution of particles within the above defined size ranges across all slots was determined. This data is provided in TABLE II and is illustrated graphically in FIG. 16.

TABLE I

Distribution of Particles in Each Slot

| Slot | Size Ranges | | | | | |
| --- | --- | --- | --- | --- | --- | --- |
| | >600 um | 600–425 um | 425–300 um | 300–180 um | 180–75 um | <75 um |
| 1 | 2.4% | 4.9% | 10.2% | 26.3% | 51.0% | 5.3% |
| 2 | 8.6% | 13.5% | 16.6% | 28.5% | 30.3% | 2.4% |
| 3 | 14.9% | 17.2% | 20.2% | 27.1% | 19.0% | 1.5% |
| 4 | 28.7% | 22.0% | 21.1% | 18.1% | 9.4% | 0.7% |
| 5 | 35.2% | 21.8% | 18.9% | 14.6% | 8.8% | 0.7% |
| 6 | 28.1% | 21.2% | 21.2% | 18.5% | 10.2% | 0.8% |
| 7 | 19.5% | 18.8% | 20.9% | 23.8% | 15.8% | 1.2% |
| 8 | 14.9% | 15.7% | 17.5% | 24.7% | 25.0% | 2.2% |
| 9 | 4.6% | 7.2% | 12.6% | 27.2% | 43.9% | 4.4% |

TABLE II

Distribution of Particles Across All Slots

Size Ranges

| Slot | >600 um | 600–425 um | 425–300 um | 300–180 um | 180–75 um | <75 um |
|---|---|---|---|---|---|---|
| 1 | 1.5% | 3.6% | 7.0% | 14.6% | 27.7% | 31.2% |
| 2 | 2.1% | 3.9% | 4.4% | 6.2% | 6.4% | 5.6% |
| 3 | 6.3% | 8.7% | 9.5% | 10.3% | 7.1% | 6.0% |
| 4 | 24.2% | 22.3% | 19.6% | 13.7% | 7.0% | 5.8% |
| 5 | 30.4% | 22.6% | 18.0% | 11.3% | 6.6% | 5.6% |
| 6 | 19.9% | 18.0% | 16.5% | 11.8% | 6.3% | 5.6% |
| 7 | 8.4% | 9.7% | 9.9% | 9.2% | 6.0% | 4.9% |
| 8 | 4.1% | 5.2% | 5.3% | 6.1% | 6.0% | 5.7% |
| 9 | 3.2% | 6.0% | 9.7% | 17.0% | 26.9% | 29.5% |

Note: "um" means microns

Figure 15:
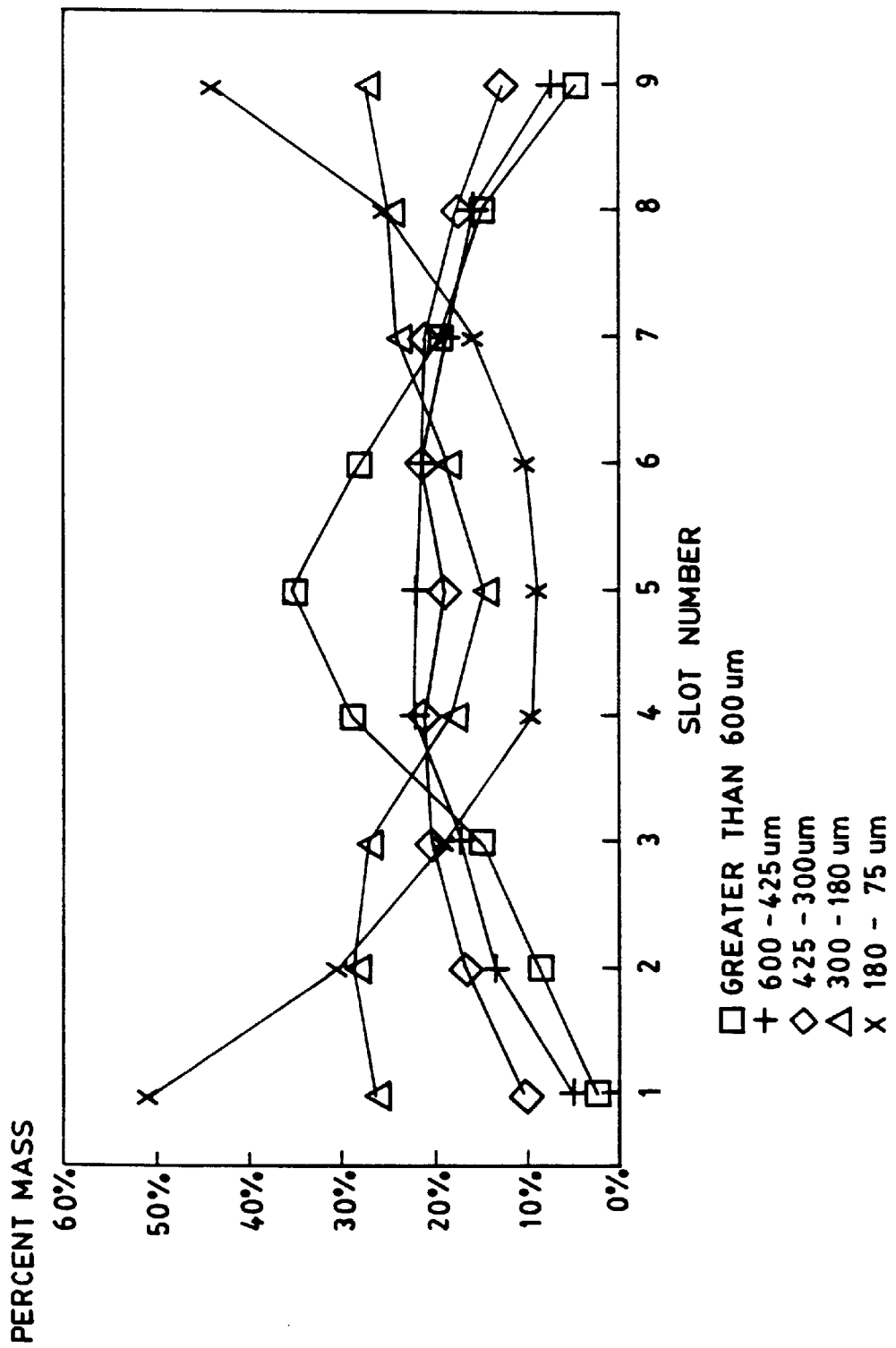
FIG. 15 is a graphic illustration of EXAMPLE 1 data.
Figure 16:
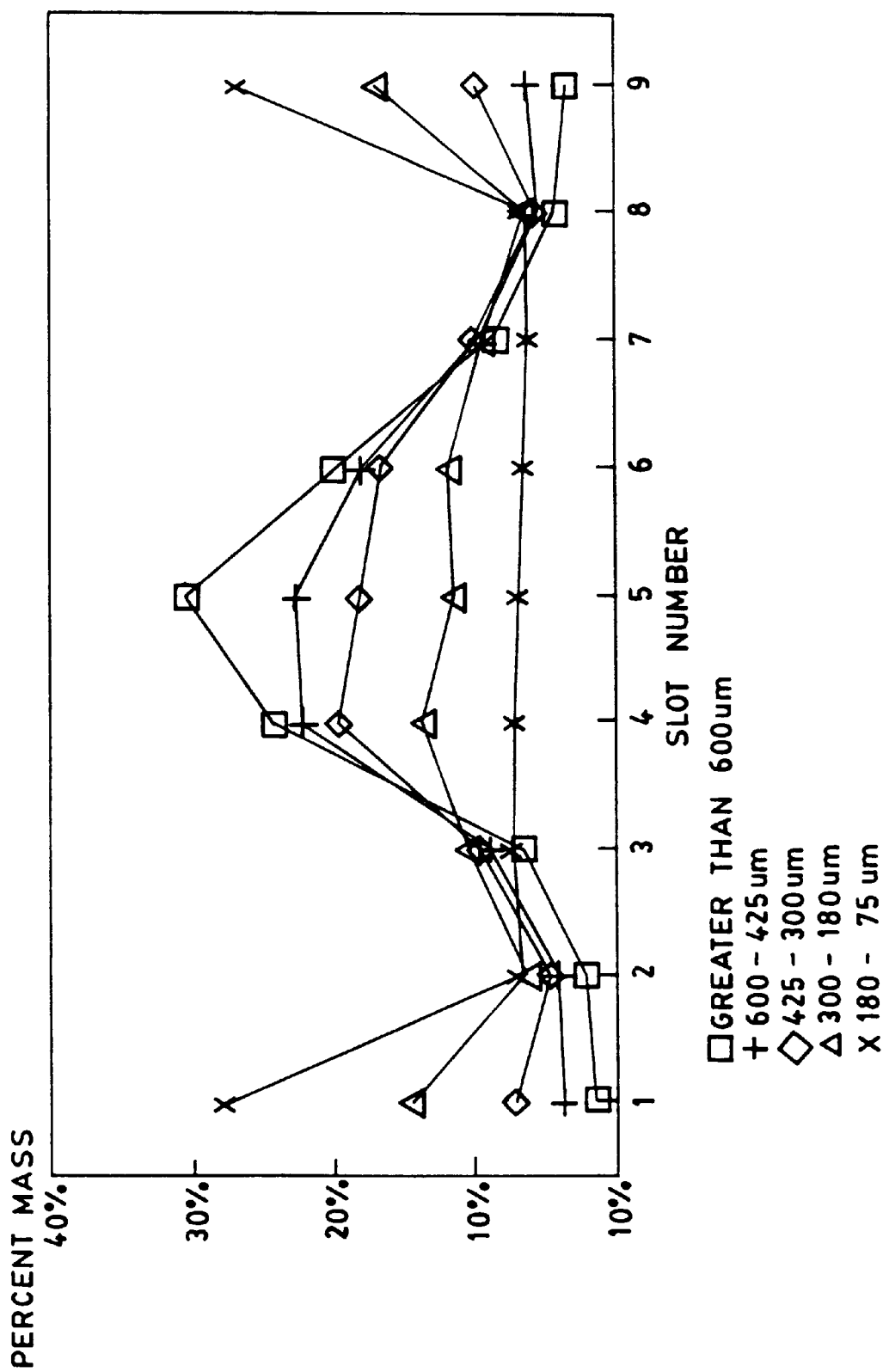
FIG. 16 is an alternate graphic illustration of EXAMPLE 1 data.

FIGS. 15 and 16 clearly establish that an absorbent particle size gradient was formed across the width of the sample tray. For example, referring now to FIG. 15, absorbent particles falling within the smallest particle size range (180 microns to 75 microns) accounted for about 50% by weight of all the absorbent particles collected in slot no. 1. On the other hand, absorbent particles falling within the largest particle size range (>600 microns) accounted for about 2% by weight of all the absorbent particles collected in slot no. 1. With continued reference to FIG. 15, absorbent particles falling within the smallest particle size range accounted for about 9% by weight of all the absorbent particles collected in slot no. 5, while absorbent particles falling within the largest particle size range accounted for about 35% by weight of all the absorbent particles collected in slot no. 5.

Referring now to FIG. 16, about 28% by weight of the absorbent particles falling within the smallest particle size range were collected in slot no. 1 and about 27% by weight of the same sized absorbent particles were collected in slot no. 9. By contrast, about 2% and 3% by weight of the absorbent particles falling within the largest particle size range were collected in slot nos. 1 and 9, respectively. As to slot no. 5, about 7% of the absorbent particles falling within the smallest particle size range were present therein, while about 30% of the absorbent particles falling within the largest particle size range were present therein.

It is understood that there are many variations which can be made to the various embodiments illustrated in FIGS. 1–16. In some circumstances, a desired result may be achieved by combining two or more of these embodiments to harness the benefits of each. In the case of absorbent gradient structures, product performance and manufacturing considerations should determine which embodiment (or combination of embodiments) is appropriate for a given situation. A plurality of electrostatic separators may also be combined, such as in series, parallel, or stacked one on top of another, to produce a multiplicity of gradient structures. As such, while the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

What is claimed is:

1. A method of making an absorbent article having a length dimension, a width dimension and a height dimension, and having a generally continuous size gradient of absorbent particles in at least one said dimension, comprising:

a. passing a population of multiple-sized absorbent particles through a gradient forming chamber;

b. subjecting the particles to a corona charge while within the gradient forming chamber; and c. applying the corona charged absorbing particles to a support layer in a generally continuous absorbent particle size gradient in at least one said dimension of the absorbent article.

2. The method of claim 1, wherein the particle size gradient dimension is expanded by increasing the corona charge.

3. The method of claim 1, wherein the particle size gradient dimension is contracted by decreasing the corona charge.

* * * * *